US006759410B1

(12) United States Patent
Adams et al.

(10) Patent No.: US 6,759,410 B1
(45) Date of Patent: Jul. 6, 2004

(54) 3,4-DIHYDRO-(1H)-QUINAZOLIN-2-ONES AND THEIR USE AS CSBP/P38 KINASE INHIBITORS

(75) Inventors: Jerry L. Adams, Wayne, PA (US); Michael J. Bower, Audubon, PA (US); Ralph Hall, Villanova, PA (US); Don Edgar Griswold, North Wales, PA (US); David C. Underwood, Ambler, PA (US)

(73) Assignee: SmithLine Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/129,889

(22) PCT Filed: Nov. 21, 2000

(86) PCT No.: PCT/US00/31908

§ 371 (c)(1),
(2), (4) Date: May 10, 2002

(87) PCT Pub. No.: WO01/37837

PCT Pub. Date: May 31, 2001

Related U.S. Application Data

(60) Provisional application No. 60/167,113, filed on Nov. 23, 1999.

(51) Int. Cl.$^7$ ..................... C07D 239/80; A61K 31/517
(52) U.S. Cl. .............................. 514/234.5; 514/266.21; 514/266.23; 514/266.31; 544/116; 544/284; 544/286
(58) Field of Search ................................. 544/116, 284, 544/286; 514/234.5, 266.21, 266.23, 266.31

(56) References Cited

U.S. PATENT DOCUMENTS

| | | | |
|---|---|---|---|
| 2,833,779 A | 5/1958 | Fields .......................... 260/296 |
| 3,707,475 A | 12/1972 | Lombardino ................. 260/309 |
| 3,772,441 A | 11/1973 | Lombardino ................. 424/273 |
| 3,929,807 A | 12/1975 | Fitzi ..................... 260/294.8 R |
| 3,940,486 A | 2/1976 | Fitzi ........................... 424/263 |
| 4,058,614 A | 11/1977 | Baldwin ...................... 424/263 |
| 4,199,592 A | 4/1980 | Cherkofsky ................. 424/273 |
| 4,447,431 A | 5/1984 | Sallmann .................... 424/246 |
| 4,503,065 A | 3/1985 | Wilkerson ................... 514/396 |
| 4,565,875 A | 1/1986 | Cavender .................... 548/336 |
| 4,686,231 A | 8/1987 | Bender et al. ............... 514/333 |
| 4,822,805 A | 4/1989 | Takasugi et al. ............ 514/341 |
| 4,886,807 A | 12/1989 | Kitamura et al. ........... 514/258 |
| 5,304,560 A | 4/1994 | Shimazaki et al. ......... 514/259 |
| 5,545,669 A | 8/1996 | Adams et al. ............... 514/562 |
| 5,559,137 A | 9/1996 | Adams et al. ............... 514/341 |
| 5,593,991 A | 1/1997 | Adams et al. ........... 514/235.2 |
| 5,593,992 A | 1/1997 | Adams et al. ........... 514/235.8 |
| 5,656,644 A | 8/1997 | Adams et al. ............... 514/341 |
| 5,658,903 A | 8/1997 | Adams et al. ........... 514/235.8 |
| 5,663,334 A | 9/1997 | Sheldrake et al. .......... 544/122 |
| 5,670,527 A | 9/1997 | Adams et al. ............... 514/341 |
| 5,686,455 A | 11/1997 | Adams et al. ............... 514/256 |
| 5,716,955 A | 2/1998 | Adams et al. ........... 514/235.8 |
| 5,716,972 A | 2/1998 | Adams et al. ............... 514/314 |
| 5,739,143 A | 4/1998 | Adams et al. ............... 514/275 |
| 5,756,499 A | 5/1998 | Adams et al. ........... 514/235.8 |
| 5,777,097 A | 7/1998 | Lee et al. .................. 536/24.31 |
| 5,783,664 A | 7/1998 | Lee et al. ..................... 530/350 |
| 5,811,549 A | 9/1998 | Adams et al. ............... 544/123 |
| 5,864,036 A | 1/1999 | Adams et al. ............... 544/123 |
| 5,869,043 A | 2/1999 | McDonnell et al. ........ 424/94.1 |
| 5,869,660 A | 2/1999 | Adams et al. ............... 544/122 |
| 5,871,934 A | 2/1999 | Lee et al. ...................... 435/7.1 |
| 5,916,891 A | 6/1999 | Adams et al. ............... 514/256 |
| 5,917,043 A | 6/1999 | Sisko .......................... 544/332 |
| 5,929,076 A | 7/1999 | Adams et al. ............... 514/252 |
| 5,955,366 A | 9/1999 | Lee et al. .................... 435/471 |
| 5,969,184 A | 10/1999 | Adams et al. ............... 564/154 |
| 5,977,103 A | 11/1999 | Adams et al. ........... 514/235.2 |
| 5,998,425 A | 12/1999 | Adams et al. ............... 514/275 |
| 6,008,235 A | 12/1999 | Adams et al. ............... 514/333 |
| 6,096,739 A | 8/2000 | Fuerstein .................. 514/235.2 |
| 6,150,373 A | 11/2000 | Harris et al. ................. 514/258 |
| 6,235,760 B1 | 5/2001 | Fuerstein ..................... 514/341 |
| 6,288,062 B1 | 9/2001 | Adams et al. ........... 514/236.8 |
| 6,335,340 B1 | 1/2002 | Gallagher et al. ..... 514/252.05 |
| 6,362,193 B1 | 3/2002 | Adams ........................ 514/274 |
| 6,528,508 B2 * | 3/2003 | Salituro et al. ........... 514/234.5 |

FOREIGN PATENT DOCUMENTS

EP 0 477 049 A1 3/1992
EP 0 477 049 B1 3/1992

(List continued on next page.)

OTHER PUBLICATIONS

Gartner et al., PubMed Abstract (Pathol. Biol. 50(2):118–26) Mar. 2002.*
Layzer, Degenerative Diseases of the Nervous System, Cecil Textbook of Medicine, 20th Edition, vol. 2, pp. 2050–2057, 1996.*
Douglas, Jr. Introduction to Viral Diseases, Cecil Textbook of Medicine, 20th Edition, vol. 2, pp. 1739–1747, 1996.*
Damasio, Alzheimer's Disease and Related Dementias, Cecil Textbook of Medicine, 20th Edition, vol. 2, pp. 1992–1996, 1996.*
Adams et al., "p38 MAP Kinase: Molecular Target for the Inhibition of Pro–inflammatory Cytokines", Progress in Medicinal Chemistry, vol. 38, pp. 1–60, 2001.

(List continued on next page.)

Primary Examiner—Deepak Rao
(74) Attorney, Agent, or Firm—Charles M. Kinzig; Stephen Venetianer; Dara L. Dinner

(57) ABSTRACT

The present invention relates to 4,4-disubstituted-3,4-dihydro-2(1H)-quinazolines of formula (1), or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

28 Claims, 4 Drawing Sheets

(2 of 4 Drawing Sheet(s) Filed in Color)

FOREIGN PATENT DOCUMENTS

| | | | |
|---|---|---|---|
| GB | 2 123 830 | 2/1984 | ......... C07D/233/64 |
| WO | WO 87/03201 | * 6/1987 | |
| WO | WO 91/19497 | 12/1991 | .......... A61K/31/44 |
| WO | WO 92/10190 | 6/1992 | .......... A61K/31/44 |
| WO | WO 92/10498 | 6/1992 | ......... C07D/487/00 |
| WO | WO 92/12154 | 7/1992 | ......... C07D/487/04 |
| WO | WO 93/14081 | 7/1993 | ......... C07D/401/04 |
| WO | WO 93/14082 | 7/1993 | ......... C07D/401/04 |
| WO | WO 94/19350 | 9/1994 | |
| WO | WO 95/02591 | 1/1995 | ......... C07D/401/04 |
| WO | WO 95/03297 | 2/1995 | ......... C07D/401/04 |
| WO | WO 95/09847 | 4/1995 | ......... C07D/239/42 |
| WO | WO 95/09851 | 4/1995 | |
| WO | WO 95/09852 | 4/1995 | ......... C07D/401/04 |
| WO | WO 95/09853 | 4/1995 | ......... C07D/401/04 |
| WO | WO 95/13067 | 5/1995 | ........... A61K/31/44 |
| WO | WO 95/31451 | 11/1995 | ......... C07D/401/04 |
| WO | WO 95/33461 | 12/1995 | |
| WO | WO 96/21452 | 7/1996 | ......... A61K/31/535 |
| WO | WO 96/21654 | 7/1996 | ......... C07D/233/00 |
| WO | WO 96/40143 | 12/1996 | ......... A61K/31/505 |
| WO | WO 97/05877 | 2/1997 | .......... A61K/31/44 |
| WO | WO 97/05878 | 2/1997 | .......... A61K/31/44 |
| WO | WO 97/12876 | 4/1997 | ......... C07D/233/76 |
| WO | WO 97/16426 | 5/1997 | ......... C07D/207/30 |
| WO | WO 97/16441 | 5/1997 | ......... C07D/401/04 |
| WO | WO 97/16442 | 5/1997 | ......... C07D/401/04 |
| WO | WO 97/23479 | 7/1997 | ......... C07D/401/14 |
| WO | WO 97/25045 | 7/1997 | ......... A61K/31/505 |
| WO | WO 97/25046 | 7/1997 | ......... A61K/31/505 |
| WO | WO 97/25047 | 7/1997 | ......... A61K/31/505 |
| WO | WO 97/25048 | 7/1997 | ......... A61K/31/505 |
| WO | WO 97/32583 | 9/1997 | .......... A61K/31/44 |
| WO | WO 97/33883 | 9/1997 | ......... C07D/401/04 |
| WO | WO 97/35855 | 10/1997 | ......... C07D/401/04 |
| WO | WO 97/35856 | 10/1997 | ......... C07D/401/04 |
| WO | WO 97/336587 | 10/1997 | .......... A61K/31/44 |
| WO | WO 97/47618 | 12/1997 | ......... C07D/403/14 |
| WO | WO 98/03484 | 1/1998 | ......... C07D/213/34 |
| WO | WO 98/06715 | 2/1998 | ......... C07D/403/06 |
| WO | WO 98/07425 | 2/1998 | .......... A61K/31/44 |
| WO | WO 98/16230 | 4/1998 | ......... A61K/31/535 |
| WO | WO 98/22109 | 5/1998 | .......... A61K/31/44 |
| WO | WO 98/22457 | 5/1998 | ......... C07D/401/04 |
| WO | WO 98/24780 | 6/1998 | ......... C07D/401/00 |
| WO | WO 98/25619 | 6/1998 | ......... A61K/31/505 |
| WO | WO 98/27098 | 6/1998 | ......... C07D/487/04 |
| WO | WO 98/28292 | 7/1998 | ......... C07D/401/00 |
| WO | WO 98/45276 | 10/1998 | ......... C07D/239/00 |
| WO | WO 98/47892 | 10/1998 | ......... C07D/401/04 |
| WO | WO 98/48799 | 11/1998 | ......... C07D/471/04 |
| WO | WO 98/52558 | 11/1998 | .......... A61K/31/34 |
| WO | WO 98/52937 | 11/1998 | ......... C07D/401/00 |
| WO | WO 98/52940 | 11/1998 | |
| WO | WO 98/52941 | 11/1998 | |
| WO | WO 98/56377 | 12/1998 | .......... A61K/31/44 |
| WO | WO 98/56788 | 12/1998 | ......... C07D/405/14 |
| WO | WO 98/57966 | 12/1998 | ......... C07D/403/02 |
| WO | WO 99/00357 | 1/1999 | |
| WO | WO 99/01130 | 1/1999 | .......... A61K/31/44 |
| WO | WO 99/01131 | 1/1999 | ......... A61K/31/445 |
| WO | WO 99/01136 | 1/1999 | .......... A61K/31/53 |
| WO | WO 99/01449 | 1/1999 | ......... C07D/401/04 |
| WO | WO 99/01452 | 1/1999 | ......... C07D/403/04 |
| WO | WO 99/03837 | 1/1999 | ......... C07D/233/54 |
| WO | WO 99/17776 | 4/1999 | ......... A61K/31/505 |
| WO | WO 99/18942 | 4/1999 | ......... A61K/31/00 |
| WO | WO 99/32110 | 7/1999 | ......... A61K/31/415 |
| WO | WO 99/32121 | 7/1999 | ......... A61K/31/505 |
| WO | WO 99/42592 | 8/1999 | ........... C12N/15/54 |
| WO | WO 99/57101 | 11/1999 | |
| WO | WO 99/57253 | 11/1999 | ............ C12N/9/00 |
| WO | WO 99/58128 | 11/1999 | .......... A61K/31/44 |
| WO | WO 99/58502 | 11/1999 | ......... C07D/213/56 |
| WO | WO 99/58523 | 11/1999 | ......... C07D/401/04 |
| WO | WO 99/59959 | 11/1999 | ......... C07C/235/56 |
| WO | WO 99/59960 | 11/1999 | ......... C07C/235/56 |
| WO | WO 99/61426 | 12/1999 | ......... C07D/235/06 |
| WO | WO 99/61437 | 12/1999 | ......... C07D/401/04 |
| WO | WO 99/61440 | 12/1999 | ......... C07D/403/14 |
| WO | WO 99/64400 | 12/1999 | |
| WO | WO 00/01688 | 1/2000 | ......... C07D/401/04 |
| WO | WO 00/06563 | 2/2000 | ......... C07D/401/04 |
| WO | WO 00/07980 | 2/2000 | ......... C07C/237/42 |
| WO | WO 00/07991 | 2/2000 | ......... C07D/213/82 |
| WO | WO 00/10563 | 3/2000 | .......... A61K/31/34 |
| WO | WO 00/12074 | 3/2000 | .......... A61K/31/00 |
| WO | WO 00/12497 | 3/2000 | ......... C07D/401/00 |
| WO | WO 00/17175 | 3/2000 | ......... C07D/277/48 |
| WO | WO 00/18738 | 4/2000 | ......... C07D/213/82 |
| WO | WO 00/19824 | 4/2000 | .......... A01N/43/42 |
| WO | WO 00/20402 | 4/2000 | ......... C07D/239/94 |
| WO | WO 00/23072 | 4/2000 | ......... A61K/31/352 |
| WO | WO 00/25791 | 5/2000 | |
| WO | WO 00/26209 | 5/2000 | ......... C07D/403/04 |
| WO | WO 00/31063 | 6/2000 | ......... C07D/401/04 |
| WO | WO00/31065 | 6/2000 | ......... C07D/401/04 |
| WO | WO 00/31072 | 6/2000 | ......... C07D/409/06 |
| WO | WO 00/35911 | 6/2000 | ......... C07D/405/14 |
| WO | WO 00/39116 | 7/2000 | ......... C07D/401/04 |
| WO | WO 00/40243 | 7/2000 | |
| WO | WO 00/41698 | 7/2000 | ......... A61K/31/535 |
| WO | WO 00/43384 | 7/2000 | ......... C07D/401/12 |
| WO | WO 00/59541 | 10/2000 | .......... A61K/45/00 |
| WO | WO 00/75131 | 12/2000 | ......... C07D/401/04 |
| WO | WO 01/00229 | 1/2001 | .......... A61K/38/19 |
| WO | WO 01/19322 | 3/2001 | |
| WO | WO 01/37837 | 5/2001 | ......... A61K/31/517 |
| WO | WO 01/38312 | 5/2001 | ......... C07D/239/80 |
| WO | WO 01/38313 | 5/2001 | ......... C07D/239/80 |
| WO | WO 01/38314 | 5/2001 | ......... C07D/239/80 |
| WO | WO 01/64679 | 9/2001 | |
| WO | WO 02/07772 | 1/2002 | .......... A61K/47/48 |
| WO | WO 02/058695 | 8/2002 | ......... A61K/31/395 |
| WO | WO 02/059083 | 8/2002 | |
| WO | WO02/060869 | 8/2002 | |

OTHER PUBLICATIONS

Lee, JC et al., P38 Mitogen–Activated Protein Kinase Inhibiotrs—Mechanism and Therapeutic Potentials, Pharmaol. Ther, 1999, vol. 82, pp. 389–397.

Goldstein, DM et al., "The discovery and development of selective Inhibitors of p38 MAP kinase from distinct chemical classes", Inflamm. Res, 2002, vol. 51, Suppl. 3, pp. S114.

Boehm et al., New inhibitors of p38 kinase, Exp. Opin. Ther. Patenst, 2000, vol. 10(1) pp. 25–37.

McKenna et al., "An Alogorithm–Directed Two–Component Library Synthesized Via Solid–Phase Methodology Yielding Potent and Orally Bioavailable p38 MAP Kinase Inhibitors", J. Med. Chem., 2002, 45, 2173–2184.

Revesz et al., "SAR of 4–Hydroxypiperidine and Hydroxyalkyl Substituted Heterocycles as Novel p38 MAP Kinase Inhibitors", Bioorganic & Medicinal Chemistry Letters 10, 2000, 1261–1264.

Gallagher et al., "2,4,5–Triarylimidazole Inhibiotrs of IL–1 Biosynthesis", Bioorganic & Medicinal Chemistry Letters, vol. 5 No. 11, pp. 1171–1176, 1995.

Gallagher et al., "Regulation of Stress–Induced Cytokine Production by Pyridinylimidazoles; Inhibition of CSBP Kinase", Bioorganic & Medicinal Chemistry, vol. 5 No. 1, pp. 49–64, 1997.

Liverton et al., "Design and Synthesis of Potent, Selective and Orally Bioavailable Tetrasubstituted Imidazole Inhibors of p38 Mitogen–Activated Protein Kinase", J. Med. Chem., 1990, 42 pp. 2180–2190.

Wilson et al., "Crystal Structure of p38 Mitogen–activated Protein Kinase", Journal of Biological Chemistry, vol. 271, No. 44 1996m pp. 27696–27700.

Wang et al., "Structural basis of inhibitor selectivity in MAP kinases", Structure, 1998, vol. 6 No. 9, pp. 1117–1128.

Cirillo et al., "The Non–Diaryl Heterocycle Classes of p38 MAP Kinase Inhibitors", Current Topics in Medicinal Chemistry, 2002, 2, pp. 1021–1035.

Jackson et al., "Pyridinylimidazole Based p38 MAP Kinase Inhibors", Current Topics in Medicinal Chemistry 2002, 2, 1011–1020.

Shewchuk et al., "Binding Mode of the 4–Anilinoquinazoline Class of Protein Kinase Inhibitor: . . . ", J. Med. Chem, 2000, 43, 133–138.

Haddad, "VX–745 Vertex Pharmaceuticals", Current Opinion in Investigational Drugs, 2001 2(8), 1070–1076.

Underwood et al., SB239063, a p38 MAPK inhibitor, reduces neutrophilia, . . . , Am J Physiol Lung Cell Mol Physiol, 279, L895–L902, 2000.

Bellon et al., "The structure of phosphorylated P38y is monomeric and reveals a conserved activation–loop conformation", Structure, Sep. 1999, 7, 1057–1065.

Hull et al., "Pathways of Inflammatory Activation in Alzheimer's Disease: Potential Targets for Disease Modifying Drugs", Current Medicinal Chemistry, 2002, 9, 83–88.

Salituro et al., Inhibitors of p38 MAP Kinase: Therapeutic Intervention in Cytokine–Mediated Diseases, Current Medicinal Chemistry, 1999, 6, 807–823.

Dinarello et al., "Proinflammatory Cytokines in Heart Disease", Blood Purif, 2001, 19, 314–321.

Sugden, "Signalling pathways in cardiac myocyte hypertrophy", The Finnish Medical Society Duodecim, Ann Med, 2001, 33, 611–622.

Lorenz et al., "Neue Therapieentwicklungen in der Rheumatoiden Arthritis", Z rheumatol, 60, 326–332, 2001.

Jarrar et al., "Inhibition of Tyrosine Kinase Signaling After Trauma–Hemmorrhage", Annals of Surgery, vol. 231, No. 3, 399–407, 2000.

Atzori et al., "Activation of the JNK/p38 pathway Occurs in Diseases Characterized by Tau Protein Pathology and is Related to Tau Phosphorylation but not to Apoptosis", Journal of Neuropatholy and Experimental Neurology, vol. 60, No. 12, Dec. 2001, 1190–1197.

Tong et al., "A highly specific inhibitor of human p38 MAP kinase binds in the ATP pocket", Nature Structural Biology, vol. 4, No. 4, Apr. 1997, 311–316.

Manson et al., "Modulation of signal–transduction pathways to chemopreventive agents", Biochem Soc. Trans., 2000, vol. 28(2), 7–12.

D'Aversa et al., "CD40–CD40L Interactions Induce Chemokine Expression by Human Microglia", American Journal of Pathology, vol. 260, No. 2, Feb. 2002, 559–567.

Lee et al.. "A protein kinase involved in the regulation of inflammatory cytokine biosynthesis", Nature, vol. 372, 22/29 Dec. 1994, 739–746.

Joyeux et al., "SB203580, a Mitogen–Activated Protein Kinase Inhibitor, Abolishes Resistance to Myocardial Infarction Induced by Heat Stress", Cardiovascular Drugs and Therapy, 2000, 14, 337–343.

Purves et al., "A role for mitogen–activated protein kinases in the etiology of diabetic neuropathy", Faseb J, 2001, 15(13), 2508–2514.

Bartlett et al., "Induction of cyclooxygenase–2 expression in human myometrial smooth muscle cells by . . . ", Journal of physiology, 1999, 520.2, 399–406.

Badger et al., "Pharmacological Profile of SB 203580, a Selective Inhibitor of Cytokine Suppressive Binding Protein/p38 Kinase, in Animals Models of Arthritis, Bone Resorption, Endotoxin shock and Immune Function", 1996, 279(3), pp. 1453–1461.

Han et al., "A MAP Kinase Targeted by Endotoxin and Hyperosmolarity in Mammalian Cells", Science, 1994, vol. 265, p. 808–811.

Barnes et al., "Future Advances in COPD Therapy", Respiration, 2001, 68, p. 441–448.

Armarego, W. J. Chem. Soc., (JCSOA9) p. 561 (1962).

Badger et al., "Protective Effect of SK&F 86002, a Novel Dual Inhibitor of Arachidonic Acid . . . ", Circulatory Shock, vol. 27, 1991, pp. 51–61 ****.

Becker et al., J. Immunol., 147, p. 4307 (1991).

Boehm et al., J. Med. Chem. 39, pp. 3929–3937 (1996).

Bradlerova et al., Chem. Zvesti, 29 (6), pp. 795–802 (1975).

Colotta et al., J. Immunol., 132(2), p. 936 (1984).

de Silva et al., J. Chem. Soc., 4, pp. 685–690, (1995).

Dinarello et al., Rev.Infect.Disease, 6, p. 51 (1984).

Dinarello, J.Clin.Immun., 5(5), p. 287–297 (1985).

Engel & Steglich, Liebigs Ann. Chem., 1916 (1978).

Ferles et al., Collect. Czech. Chem. Commun., 5 (46), pp 1167–1172 (1981).

Fischer et al., Rec.Trav.Chim.Pays.Bas., 84, p.439 (1965).

Fulmer et al., J. Heterocycl. Chem., 17 (4), pp. 799–800 (1980).

Gallahger et al., Bioorganic & Medicinal Chem., vol. 5, No. 1, pp. 49–64 (1997).

Garigipati, R., Tetrahedron Letters, 31,p.190 (1989).

Gilbert, Synthesis, pp. 30–32 (1972).

Griswold et al., "Differentiation in vivo of classical non–steroidal antiinflammatory drugs . . . ", Drugs Exptl. Clin. Res., XIX(6), 1993, pp. 243–248.

Griswold et al., "Effect of Inhibots of Eicosanoid Metabolism in Murine Collagen–Induced Arthritis", Arthritis and Rheumatism, vol. 31 No. 11, Nov. 1998, pp. 1406–1412.

Ishibashi, Chem. Pharm. Bull., 37(8), pp. 2214–2216 (1989).

Johnson, P.A., J.Chem.Soc., Perkin Trans., vol. 1, pp. 895–905 (1996).

Jurkowski–Kowalczyk, Rocz. Chem., 51 (6), pp. 1191–9 (1977).

Katritzky, Synthesis, pp. 45–47 (1993).

Kawasaki et al., J. Bio. Chem., 272(30), pp. 18518–18521.

Kumada et al., Tetrahedron Letters, 22, p. 5319 (1981).

Lamartina et al., Boll. Chim. Farm., 129 (12), pp. 314–316 (1990).

Lee et al., "Bicyclic Imidazoles as a Novel Class of Cytokine Biosynthesis Inhibitors", Annals NY Academy of Sciences, vol. 696, 1993, pp. 149–170.

Makailu et al., Zh. Obshch. Khim., 56 (7), pp. 1513–1517 (1986).

Morton et al., Tetrahedron Letters, 4123 (1982).

Olivera et al., "Beneficial Effects of SK&F 105809, a Novel Cytokine–Suppressive Agent, in Murine Models of Endotoxin Shock", Circulatory Shock, 37, 1992, pp. 301–306.

Poli et al., Proc. Nat'l Acad.Sci., 87, p. 782–784 (1990).

Pridgen, J.Org.Chem., 47, p. 4319 (1982).

Protecting Groups in Organic Synthesis, Second Edition, Greene TW and Wuts PGM, Wiley–Interscience, New York 1991, pp. 10–174 (hydroxyl and phenolic) and pp. 309–403 (NH protection).

R.P.Soni, Aust.J.Chem., 35, p.1493–6 (1982).

Santilli et al., "Thieno[2,3–d]pyrimidines. I. A New Method for the Preparation of Esters . . . ", J. Heterocycl Chem., vol. 8, 1971, pp. 445–453.

Simon et al., J. Immunol. Methods, 84, p. 85 (1985).

Snieckus, V., Tetrahedron Letters, 29, 2135 (1988).

Stille, J.Amer.Chem.Soc., 109, p. 5478 (1978).

Strzybny et al., J. Org. Chem., 28, p. 3381 (1963).

Szucs et al., Chem. Zvesti, 26 (4), pp. 354–359 (1972).

Szucs et al., Acta fac. Pharm. Univ. Commenianae, 30, pp. 127–146 (1977).

Terashimia, M., Chem.Pharm.Bull., 11, p. 4755 (1985).

Thompson, W.J., et al., J.Org.Chem., 49, p. 5237 (1984).

Uno, Bull. Chem. Soc. Japan., vol. 69, pp. 1763–1767 (1996).

VanLeusen et al., J.O.C., 42, p. 1153 (1977).

Vartanyan et al., 40, (9), pp. 552–560 (1987).

Votta et al., "Inhibition of Human Monocyte IL–1 Production by SK&F 86002", Int. J. Immunotherapy, VI(1), 1990, pp. 1–12.

Warrior et al., "Development of p38 Kinase Binding Assay for Hight Throughput Screening", Journal of Biomolecular Screening, vol. 4 No. 3, 1999, pp. 129–135.

Wilson et al., Chemistry & Biology, vol. 4, No. 6, pp 423–431 (1997).

Zavyalov, et al., Khim Farm Zh, 26(3), p. 88 (1992) (With Translation).

* cited by examiner

3,4-DIHYDRO-(1H)-QUINAZOLIN-2-ONES AND THEIR USE AS CSBP/P38 KINASE INHIBITORS

This application is the §371 national stage entry of PCT/US/00/31908, filed Nov. 21, 2000, which claims benefit from provisional application U.S. Ser. No. 60/167,113 filed Nov. 23, 1999.

FIELD OF THE INVENTION

This invention relates to a novel group of 5-aryl-3,4-dihydro-(1H) quinazolin-2-one compounds, processes for the preparation thereof, the use thereof in treating CSBP/p38 kinase mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e. g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995);Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). The first indications suggesting that the signal transduction pathway leading to LPS-induced cytokine biosynthesis involved protein kinases came from studies of Weinstein [Weinstein, et al., J. Immunol. 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N. Y. Acad. Sci., 696, 149 (1993)].

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 1). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. Trends Cell Biol., 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, J. Clinical Immunology, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds that are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera* 279 (3): 1453–1461 (1996); Griswold, et al, *Pharmacol. Comm.* 7,323–229 (1996)].

There remains a need for treatment, in this field, for compounds which are cytokine suppressive anti-inflammatory drugs, i.e. compounds which are capable of inhibiting the CSBP/p38/RK kinase.

BRIEF DESCRIPTION OF THE DRAWINGS

The patent application filed contains at least one drawing executed in color. Copies of this patent or patent application publication with color drawing(s) will be provided by the Patent & Trademark Office upon request and payment of necessary fee.

SUMMARY OF THE INVENTION

Figure 1:
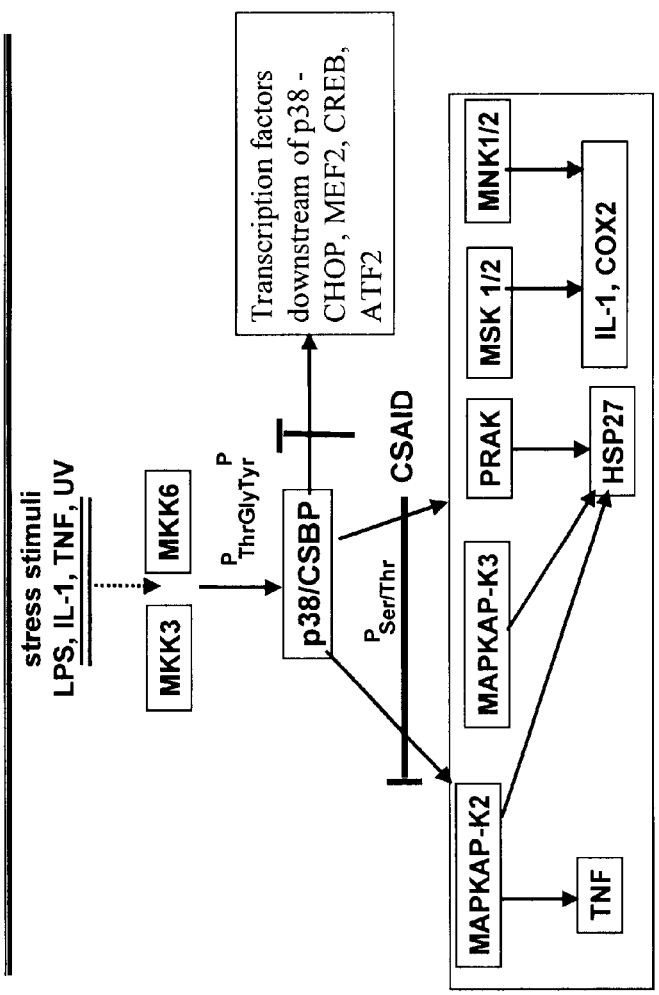
FIG. 1 demonstrates the p38 kinase cascade.

This invention relates to the novel compounds of Formula (I), and pharmaceutical compositions comprising a compound of Formula (I), and a pharmaceutically acceptable diluent or carrier.

This invention relates to a method of treating a CSBP/RK/p38 kinase mediated disease in a mammal in need thereof, which comprises administering to said mammal an effective amount of a compound of Formula (I).

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-6 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides a compound of Formula (I):

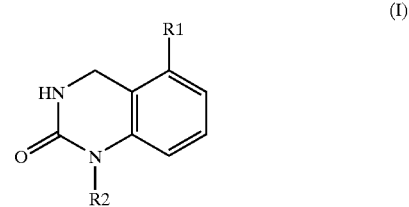

wherein $R_1$ is phenyl, naphth-1-yl, naphth-2-yl, heterocyclic or heteroaryl ring, which ring is optionally substituted independently by one to three substituents selected from halogen, $C_{1-4}$ alkyl, halo-substituted-$C_{1-24}$ alkyl, cyano, nitro, $(CR_{10}R_{20})_v NR_4R_{14}$, $(CR_{10}R_{20})_v C(Z)NR_4R_{14}$, $(CR_{10}R_{20})_v C(Z)OR_8$, $(CR_{10}R_{20})_v COR_3$, $(CR_{10}R_{20})_v C(O)H$, $SR_5$, $S(O)R_5$, $S(O)_2R_5$, $(CR_{10}R_{20})_v OR_8$, $ZC(Z)R_{11}$, $NR_{10}C(Z)R_{11}$, or $NR_{10}S(O)_2R_7$;

$R_2$ is a $C_{1-10}$ alkyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, heterocyclic, or heterocyclyl$C_{1-10}$ alkyl moiety, which moieties are optionally substituted one or more times independently with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_n OR_6$, $(CR_{10}R_{20})_n SH$, $(CR_{10}R_{20})_n S(O)_m R_7$, $(CR_{10}R_{20})_n NHS(O)_2 R_7$, $(CR_{10}R_{20})_n NR_4R_{14}$, $(CR_{10}R_{20})_n CN$, $(CR_{10}R_{20})_n S(O)_2 NR_4R_{14}$, $(CR_{10}R_{20})_n C(Z)R_6$, $(CR_{10}R_{20})_n OC(Z)R_6$, $(CR_{10}R_{20})_n C(Z)OR_6$, $(CR_{10}R_{20})_n C(Z)NR_4R_{14}$, $(CR_{10}R_{20})_n NR_{10}C(Z)R_6$, $(CR_{10}C_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$;

$R_3$ is $C_{1-4}$ alkyl, halo-substituted $C_{1-4}$ alkyl, $C_{1-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vNHS(O)_2R_7$, or $(CR_{10}R_{20})_vNR_4R_{14}$; and wherein the aryl, arylalkyl, heteroaryl, heteroaryl alkyl may be optionally substituted;

$R_4$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_5$ is hydrogen, $C_{1-4}$ alkyl, $C_{2-4}$ alkenyl, $C_{2-4}$ alkynyl or $NR_4R_{14}$, excluding the moieties $SR_5$ being $SNR_4R_{14}$, $S(O)_2R_5$ being $SO_2H$ and $S(O)R_5$ being SOH;

$R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein these moieties may be optionally substituted;

$R_7$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted;

$R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_t NHS(O)_2R_7$, or $(CR_{10}R_{20})_tNR_4R_{14}$; and wherein the aryl, arylalkyl, heteroaryl, heteroaryl alkyl may be optionally substituted;

$R_9$ is hydrogen, $C(Z)R_6$ or optionally substituted $C_{1-10}$ alkyl, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_vNR_4R_{14}$;

and wherein the aryl, arylalkyl, heteroaryl, heteroaryl alkyl may be optionally substituted;

Z is oxygen or sulfur;

n is 0, or an integer having a value of 1 to 10;

m is 0, or the integer 1 or 2;

v is 0, or an integer having a value of 1 or 2;

t is an integer having a value of 1 to 3;

or a pharmaceutically acceptable salt thereof.

DETAILED DESCRIPTION OF THE INVENTION

The present invention is directed to novel compounds of Formula (I), or pharmaceutically acceptable salts thereof.

Suitably, for compounds of Formula (I) $R_1$ is phenyl, naphth-1-yl, naphth-2-yl, heterocyclic or a heteroaryl ring. The $R_1$ moiety may be optionally substituted independently by one or more substituents, preferably from one to three substituents each independently selected from halogen, $C_{1-4}$ alkyl, halo-substituted-$C_{1-4}$ alkyl, cyano, nitro, $(CR_{10}R_{20})_vNR_4R_{14}$, $(CR_{10}R_{20})_vC(Z)NR_4R_{14}$, $(CR_{10}R_{20})_vC(Z)OR_8$, $(CR_{10}R_{20})_vCOR_3$, $(CR_{10}R_{20})_vC(O)H$, $SR_5$, $S(O)R_5$, $S(O)_2R_5$, $(CR_{10}R_{20})_vOR_8$, $ZC(Z)R_{11}$, $NR_{10}C(Z)R_{11}$, or $NR_{10}S(O)_2R_7$.

Preferably, the $R_1$ moiety is an aryl ring. More preferably, the aryl ring is a phenyl ring.

Preferably, the $R_1$ moiety is substituted by one or more halogens, such as fluorine or chlorine; an alkyl, hydroxy, alkoxy, amino, or halosubstituted alkyl, such as $CF_3$.

Suitably, for compounds of Formula (I), $R_2$ is an $C_{1-10}$ alkyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, heterocyclic, or heterocyclyl$C_{1-10}$ alkyl moiety. These moieties may be optionally substituted one or more times, preferably 1 to 3 times, independently with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}C_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Preferably, $R_2$ is an optionally substituted aryl or arylalkyl moiety, such as a unsubstituted or substituted phenyl or benzyl ring; a $C_{1-10}$ alkyl, such as isopropyl; $C_{3-7}$ cycloalkyl, such as cyclohexyl; a heteroarylalkyl, such as an optionally substitued pyrrolidinyl $C_{1-10}$ alkyl or pyridyl $C_{1-10}$ alkyl; or an optionally substituted heterocyclic $C_{1-10}$ alkyl, such as a morpholinyl $C_{1-10}$ alkyl. The alkyl portion of these chains may as indicated herein be a branced or straight chain.

Preferably the $R_2$ moiety is substituted by one or more halogens, such as fluorine or chlorine; an alkyl, such as methyl; hydroxy, alkoxy, amino, or a halosubstituted alkyl, such as $CF_3$.

Preferred $R_2$ moieties include phenyl, benzyl, phenylethyl, cyclohexyl, isopropyl, optionally substitued pyrrolylethyl, 2,6-difluorphenyl, 2-morpholin-4-yl-propyl, 2-morpholin-4-yl-ethyl, or 2-pyridinylethyl.

A preferred substition pattern on the $R_2$ ring when it is a phenyl or phenylalkyl moiety is in the 2,6-position.

Suitably, n is 0, or an integer having a value of 1 to 10.

Suitably, m is 0, or the integer 1 or 2.

Suitably, v is 0, or an integer having a value of 1 or 2.

Suitably, t is an integer having a value of 1 to 3.

Suitably, Z is oxygen or sulfur, preferably oxygen.

Suitably, $R_3$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vNHS(O)_2R_7$, or $(CR_{10}R_{20})_v NR_4R_{14}$; and wherein the aryl, arylalkyl, heteroaryl, heteroaryl alkyl may be optionally substituted.

Suitably, $R_4$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ being $SNR_4R_{14}$, $S(O)_2R_5$ being $SO_2H$ and $S(O)R_5$ being $SOH$.

Suitably, $R_6$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or heteroaryl$C_{1-10}$ alkyl, wherein these moieties may be optionally substituted.

Suitably, $R_7$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_nOR_7$, $(CR_{10}R_{20})_nS(O)_mR_7$, $(CR_{10}R_{20})_nNHS(O)_2R_7$, or $(CR_{10}R_{20})_nNR_4R_{14}$; and wherein the aryl, arylalkyl, heteroaryl, heteroaryl alkyl may be optionally substituted.

Suitably, $R_9$ is hydrogen, $C(Z)R_6$ or optionally substituted $C_{1-10}$ alkyl, optionally substituted aryl or optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_nOR_7$, $(CR_{10}R_{20})_nS(O)_mR_7$, $(CR_{10}R_{20})_nNHS(O)_2R_7$, or $(CR_{10}R_{20})_v NR_4R_{14}$; and wherein the aryl, arylalkyl, heteroaryl, heteroaryl alkyl may be optionally substituted.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; $S(O)m$ alkyl, such as methyl thio, methylsulfinyl or methyl sulfonyl; $NR_7R_{17}$, such as amino or mono or -disubstituted $C_{1-4}$ alkyl or wherein the $R_7R_{17}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; $S(O)_m$ alkyl; amino, mono & di-substituted $C_{1-4}$ alkyl amino, such as in the $NR_7R_{17}$ group; $C_{1-4}$ alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "$C_{1-10}$alkyl" or "alkyl" or "alkyl$_{1-10}$" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl.

The term "heteroaryl" (on its own or in any combination, such as "heteroaryloxy", or "heteroaryl alkyl") is used herein to mean a 5–10 membered aromatic ring system in which one or more rings contain one or more heteroatoms selected from the group consisting of N, O or S, such as, but not limited to, The term "heterocyclic" (on its own or in any combination, such as "heterocyclylalkyl") is used herein to mean a saturated or partially unsaturated 4–10 membered ring system in which one or more rings contain one or more heteroatoms selected from the group consisting of N, O, or S, such as, but not limited to, pyrrolidine, piperidine, piperazine, morpholine, tetrahydropyran, imidazolidine, or pyrazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

The term "sulfinyl" is used herein to mean the oxide S (O) of the corresponding sulfide, the term "thio" refers to the sulfide, and the term "sulfonyl" refers to the fully oxidized S (O)$_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean C(O)$C_{1-10}$ alkyl wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I), according to the invention include those mentioned in the Examples and their pharmaceutically acceptable salts.

The compounds of Formula (I) may be obtained by applying synthetic procedures, described herein. The synthesis provided for is applicable to producing compounds of Formula (I) having a variety of different $R_1$, and $R_2$, groups which are reacted, employing optional substituents which are suitably protected, to achieve compatibility with the reactions outlined herein. Subsequent deprotection, in those cases, then affords compounds of the nature generally disclosed.

Once the nucleus has been established, further compounds of Formula (I) may be prepared by applying standard techniques for functional group interconversion, well known in the art. For instance: C(O)NR$_4$R$_{14}$ from CO$_2$CH$_3$ by heating with or without catalytic metal cyanide, e.g. NaCN, and HNR$_4$R$_{14}$ in CH$_3$OH; OC(O)R$_3$ from OH with e.g., ClC(O)R$_3$ in pyridine; NR$_{10}$—C(S)NR$_4$R$_{14}$ from NHR$_{10}$ with an alkylisothiocyante or thiocyanic acid; NR$_{10}$C(O)OR$_7$ from NHR$_{10}$ with the alkyl chloroformate; NR$_{10}$C(O)NR$_4$R$_{14}$ from NHR$_{10}$ by treatment with an isocyanate, e.g. HN=C=O or R$_{10}$N=C=O; NR$_{10}$—C(O)R$_7$ from NHR$_{10}$ by treatment with Cl—C(O)R$_7$ in pyridine; C(=NR$_{10}$)NR$_4$R$_{14}$ from C(NR$_4$R$_{14}$)SR$_3$ with H$_3$NR$_3$$^+$OAc$^{31}$ by heating in alcohol; C(NR$_4$R$_{14}$)SR$_3$ from C(S)NR$_4$R$_{14}$ with R$_6$-I in an inert solvent, e.g. acetone; C(S)NR$_4$R$_{14}$ (where R$_4$ or R$_{14}$ is not hydrogen) from C(S)NH$_2$ with HNR$_4$R$_{14}$—C(=NCN)—NR$_4$R$_{14}$ from C(=NR$_4$R$_{14}$)—SR$_3$ with NH$_2$CN by heating in anhydrous alcohol, alternatively from C(=NH)—NR$_4$R$_{14}$ by treatment with BrCN and NaOEt in EtOH; NR$_{10}$—C(=NCN)SR$_8$ from NHR$_{10}$ by treatment with (R$_8$S)2C=NCN; NR$_{10}$SO$_2$R$_3$ from NHR$_{10}$ by treatment with ClSO$_2$R$_3$ by heating in pyridine; NR$_{10}$C(S)R$_6$ from NR$_{10}$C(O)R$_6$ by treatment with Lawesson's reagent [2,4-bis(4-methoxyphenyl)-1,3,2,4-dithiadiphosphetane-2,4-disulfide]; NR$_{10}$SO$_2$CF$_3$ from NHR$_6$ with triflic anhydride and base wherein R$_3$, R$_6$, R$_7$, R$_{10}$, R$_4$ and R$_{14}$ are as defined in Formula (I) herein.

Precursors of the groups R$_1$, and R$_2$ can be other R$_1$, and R$_2$ groups which can be interconverted by applying standard techniques for functional group interconversion. For example wherein a moiety is a halo substituted C$_{1-10}$ alkyl can be converted to the corresponding C$_{1-10}$ alkylN$_3$ derivative by reacting with a suitable azide salt, and thereafter if desired can be reduced to the corresponding C$_{1-10}$alkylNH$_2$ compound, which in turn can be reacted with R$_7$S(0)$_2$X wherein X is halo (e.g., chloro) to yield the corresponding C$_{1-10}$alkylNHS(0)$_2$R$_7$ compound.

Alternatively wherein the moiety is a halo-substituted C$_{1-10}$-alkyl it can be reacted with an amine R$_4$R$_{14}$NH to yield the corresponding C$_{1-10}$-alkylNR$_4$R$_{14}$ compound, or can be reacted with an alkali metal salt of R$_7$SH to yield the corresponding C$_{1-10}$alkylSR$_7$ compound.

Suitable protecting groups for use with hydroxyl groups and nitrogen groups are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, (CR$_{10}$R$_{20}$)$_n$.

Pharmaceutically acid addition salts of compounds of Formula (I) may be obtained in known manner, for example by treatment thereof with an appropriate amount of acid in the presence of a suitable solvent.

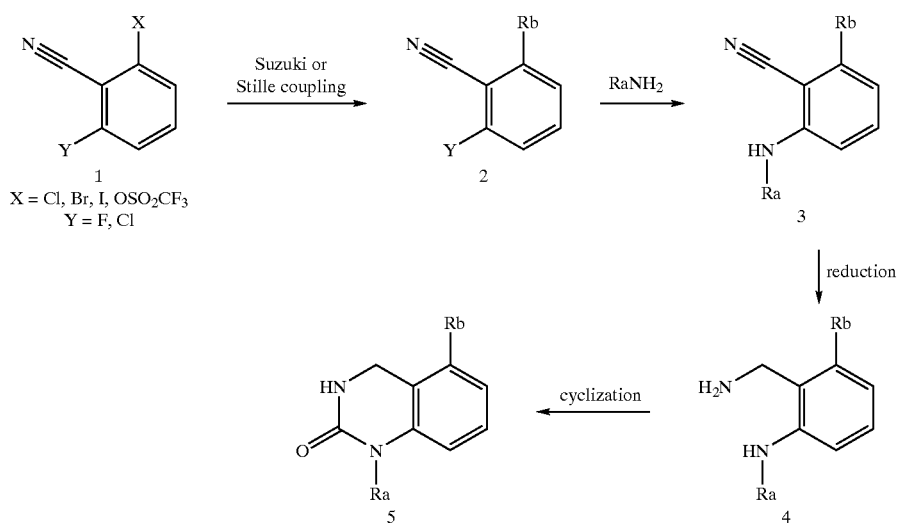

For purposes herein in Scheme 1, Ra and Rb are as defined in Formula (I) as R$_2$ and R$_1$ respectively.

Synthesis of 3,4-Dihydro-(1H)-quinazolin-2-ones substituted with an aryl or heteroaryl substituent in the 5 position (Rb) can be prepared by starting from a suitable 2,3 disubstituted benzonitrile (1). Some of these benzonitriles are commercially available while others can be prepared from commercially available 2-amino-6-halobenzonitriles following literature procedures such as that exemplified by Hynes, John B. et. al., J. Hetercycl. Chem. 1988, 25, 1173–1177. Reaction of (1) with a boronic acid or derivative under typical aryl coupling conditions such as the Suzuki reaction described in Miyaura and Suzuki, Chem. Rev. 1995, 95, 2547–2483 gives the cross-coupling product (2). Many of the required boronic acids or their derivatives are commercially available and others can be prepared by methods outlined in Miyaura and Suzuki, Chem. Rev. 1995, 95, 2547–2483. The cross coupled products (2) can also be prepared by a Stille cross-coupling reaction as outlined in Mitchell, T. N., Synthesis 1992, 803–815. Reaction of coupled product (2) with an appropriate primary amine, aniline, or heteroaryl amine, many of which are commercially available, in a suitable solvent such as dimethyl sulfoxide or dimethylformamide will give the secondary amine (3). In cases of aliphatic amines, the amine should generally have sufficient nucleophilicity to displace the halide without addition of a stronger base to form the amine anion as demonstrated in Hynes, John B. et. al., J. Hetercycl. Chem. 1988, 25, 1173–1177. In the case of the aromatic amines such as aniline, preforming the anion by the use of a strong base such as sodium hydride or potassium t-butoxide should facilitate the reaction as to exemplified in Mettey, Yvette et. al., *Heterocycles*, 1993, 36, 987–993, and Govin, John H., *J. Chem. Soc., Perkin Trans.* 1, 1988, 6, 1331–1335. Reduction of the nitrile (3) to give the benzyl amine (4) can be accomplished with a variety of reducing agents such as lithium aluminum hydride in a suitable solvent such as diethyl ether or tetrahydrofuran at temperatures ranging from 0° C. to reflux. Reduction of the nitrile to the amine may also be carried out by hydrogenation over a variety of catalysts such as Raney nickel, platinum or palladium in a suitable solvent such as ethanol, methanol, ethyl acetate, or acetic acid. Alternatively the reduction could be carried out using any of the appropriate boranes or borohydride reducing agents in a suitable solvent such as tetrahydrofuran or diethyl ether. Cyclization of the diamino compound (4) to the desired 3,4-dihydro-(1H)-quinazolin-2-ones (5), can be accomplished by a variety of synthetic procedures only a few of which are exemplified here. Cyclization can be accomplished using 1,1'-carbonyldiimidazole as demonstrated in Takai, Haruki et. al., *Chem. Pharm. Bull.*, 1985, 33, 1116–1128. Cyclization can also be carried out with phosgene as demonstrated by Szabo, Janos, et. al., *J. Heterocycl. Chem.* 1992, 29, 1513–1517. Alternatively, cyclization can be carried out using chloroformates as exemplified in Kornet, Milton, *J. Heterocycl. Chem.* 1992,29, 103–105.

Methods of Treatment

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic. arthritis, Reiter's syndrome, rheumatoid arthritis, gout, traumatic arthritis, rubella arthritis and acute synovitis. Recent evidence also links IL-1 activity to diabetes, pancreatic β cell diseases and Alzheimer's disease.

Use of a CSAID for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructive pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol 26, p 840; Teren et al. (1997), Am J Respir Crit Care Med vol 155, p1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the, veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8; or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in
 (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. These inhibitors are of aid in determining the signaling pathway involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, chronic renal failure, angiogenesis & related processes, such as cancer, thrombosis, glomerulonephritis, diabetes and pancreatic b cells, multiple sclerosis, muscle degeneration , eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). B *Ann. N. Y. Acad. Sci.* 696, 149–170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Another aspect of the present invention is directed to the treatment of inhaled smoke induced airway inflammation, lung chemokine production and cytokine production. The invention may be directed to treatment of the airway induced inflammation which is secondary to other respiratory disorders such as viral infections that exacerbate asthma (induced by such infections), chronic bronchitis, chronic obstructive pulmonary disease, otitis media, and sinusitis. A respiratory viral infection treated in conjunction with the smoke related airway inflammation may also be associated with a secondary bacterial infection, such as otitis media, sinusitis, or pneumonia.

It is noted that the inflammation may be due to cytokines and chemokine release from neutrophile activation and other leukocytes, as well as vascular and airway endothelial cell activiation.

For use herein treatment may include prophylaxis for use in a treatment group who may be susceptible to such airway inflammation. It may also include reducing the symptoms of, ameliorating the symptoms of, reducing the severity of, reducing the incidence of, or any other change in the condition of the patient, which improves the therapeutic outcome.

Suitable patient populations for whom this may be prophylatically beneficial could be firemen who routinely inhale smoke in the course of their duties; use in the military, and by civilians in wartime exposure.

As noted, smoke of natural causes, such as plant extracts, natural plants products, synthetic material, chemically treated natural materials, or natural products such as oil and gas or other fossil fuels, may be treated within the scope of this invention. Suitably, the treatment including prophylaxis is related to cigarette smoke or synthetic/composites, such as occur in fires associated with buring buildings or homes.

Another aspect of the present invention relates to the use of a CSBP/p38 kinase inhibitor for the treatment, including prophylaxis, of the hypertussive activity associated withwith resulting airway inflammation and/or cough in a mammal in need thereof.

The present invention also relates to use of a CSBP/p38 kinase inhibitor for the treatment, including prophylaxis, of the inflammation enhanced cought related disorders in a mammal in need thereof.

The present invention is also directed to the use of a compound of Formula (I) in eosinophilic bronchitis, and in cough variant asthma.

The compounds of Formula (I) may also be used in the treatment, including prophylaxis, of eosinophilic inflammation in the airways and cough. Treatment, including prophylaxis is appropriate for eosinophilic bronchitis (as this differs from asthma) and for the treatment, including prophylaxis of cough variant asthma. These disorders may be directed to treatment of the airway induced inflammation which is secondary to other respiratory disorders such as viral infections that exacerbate asthma (induced by such infections), chronic bronchitis, chronic obstructive: pulmonary disease, otitis media, and sinusitis. A respiratory viral infection treated in conjunction with the smoke related airway inflammation may also be associated with a secondary bacterial infection, such as otitis media, sinusitis, or pneumonia.

The hypertussive or inflammation enhanced cough related disorders may either be a direct result of or an association with eosinophilia activity. It may also be a result of, or associated with the blocking production of certain cytokines which may mediate these phenomena.

For use herein treatment may include prophylaxis for use in a treatment group who may be susceptible to such airway inflammation, and/or cough. It may also include reducing the symptoms of, ameliorating the symptoms of, reducing the severity of, reducing the incidence of, or any other change in the condition of the patient, which improves the therapeutic outcome.

Clinically, eosinophilic bronchitis presents as chronic cough and sputum eosinophilia, but without the abnormalities of airway function seen in asthma. In contrast to cough in patients without sputum eosinophilia, the cough responds to anti-inflammatory therapy, such as inhaled corticosteroids (Niimi et al., Eosinophilic inflammation in cough variant asthma, European Respiratory Journal. 11 (5): 1064–9, (1998)).

Patients with cough-variant asthma may also have the following criteria: (1) have not been previously diagnosed as having asthma; (2) complain of a cough of at least a 3-week duration; (3) do not complain of wheezing, shortness of breath, or chest tightness; (4) have normal results of physical examinations; (5) have normal or nearly normal results of spirometry; (6) have evidence of bronchial hyperresponsiveness during bronchoprovocation challenge testing; and (7) have a favorable response to asthma medications (Irwin et al., Interpretation of positive results of a methacholine inhalation challenge and 1 week of inhaled bronchodilator use in diagnosing and treating cough-variant asthma (Archives of Internal Medicine. 157(17):1981–1987, (1997)).

Unlike conventional anti-tussive agents, such as codeine or dextromethorphan, a p38 kinase inhibitor appears to have no direct antitussive activity, but reduces the airway eosinophilia and normalizes the hypertussive state. Therefore, use of a p38 inhibitor will reduce the added coughs, or hypertussive state, back to a normal level which can be suitably treated with conventional agents and/or therapies as appropriate. Use of the p38 inhibitors will allow for the maintenance of patients who are subject to increased cough responsiveness, especially unproductive cough, due to other underlying disorders or treatments. This increased cough responsiveness may be modulated, or decreased by use of this innovative anti-inflammatory therapy.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically; active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The invention will now be described by reference to the following biological examples which are merely illustrative and are not to be construed as a limitation of the scope of the present invention.

Biological Examples

The cytokine-inhibiting effects of compounds of the present invention may be determined by the following in vitro assays:

Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (IL-4) to secrete IL-2, in concert with A23187 ionophore) or the method of Lee et al., J. ImmunoTherapy, 6 (1), 1–12 (1990) (ELISA assay).

In vivo TNF Assay:

Suitable assays may be found in:

(1) Griswold et al., *Drugs Under Exp. and Clinical Res.,XIX* (6), 243–248 (1993); or (2) Boehm, et al., Journal Of Medicinal Chemistry 39, 3929–3937 (1996) whose disclosures are incorporated by reference herein in their entirety.

LPS-induced TNFα Production in Mice and Rats

In order to evaluate in vivo inhibition of LPS-induced TNF(x production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at $-20°$ C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat anti-rabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at –80 C.

Cytokine measurement: IL-1 and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay:

This assay measures the CSBP/p38-catalyzed transfer of $^{32}p$ from [a-$^{32}$P]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSBP Kinase", BioOrganic & Medicinal Chemistry, 1997, 5, 49–64).

Reactions were carried in round bottom 96 well plate (from Corning) in a 30 ml volume. Reactions contained (in final concentration): 25 mM Hepes, pH 7.5; 8 mM $MgCl_2$; 0.17 mM ATP (the $Km_{[ATP]}$ of p38 (see Lee et al., Nature 300, n72 pg. 639–746 (Dec. 1994)); 2.5 uCi of [g-32P]ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hours of incubation. The kinase activity values were obtained after subtracting values generated in the absence of substrate which were 10–15% of total values.

Representative compounds of Formula (I), Examples 1 to 14 all demonstrated positive inhibitory activity of an $IC_{50}$ of <50 uM in this kinase assay or a similar binding assay.

Prostaglandin Endoperoxide Synthase-2 (PGHS-2) Assay:

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593,992 whose disclosure is incorporated herein by reference.

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

Rhinovirus Methods:

Cell lines, rhinovirus serotype 39, and influenza virus A/PR/8/34 are purchased from American Type Culture Collection (ATCC). BEAS-2B cells were cultured according to instructions provided by ATCC using BEGM (bronchial epithelial growth media) purchased from Clonetics Corp. HELA cell cultures, used for detection and titration of virus, are maintained in Eagle's minimum essential media containing 10% fetal calf serum, 2 mM 1-glutamine, and 10 mM HEPES buffer (MEM).

A modification of the method reported by Subauste et al., Supra, for in vitro infection of human bronchial epithelial cells with rhinovirus is used in these studies. BEAS-2B cells ($2 \times 10^5$/well) are cultured in collagen-coated wells for 24 hours prior to infection with rhinovirus. Rhinovirus serotype 39 is added to cell cultures for one hour incubation at 34° C. after which inoculum is replaced with fresh media and cultures are incubated for an additional 72 hours at 34° C. Supernatants are collected at 72 hours post-infection and are assayed for cytokine protein concentration by ELISA using commercially available kits (R&D Systems). Virus yield is also determined from culture supernatants using a microtitration assay in HELA cell cultures (Subauste et al., supra 1995). In cultures treated with p38 kinase inhibitors, drug is added 30 minutes prior to infection. Stocks of compounds are prepared in DMSO (10 mM drug) and stored at −20° C.

For detection of p38 kinase, cultures are incubated in basal media without growth factors and additives to reduce endogenous levels of activated p38 kinase. Cells are harvested at various timepoints after addition of rhinovirus. Detection of tyrosine phosphorylated p38 kinase by immunoblot is analyzed by a commercially available kit and is performed according to the manufacturer's instructions (PhosphoPlus p38 MAPK Antibody Kit: New England BioLabs Inc.).

In some experiments, BEAS-2B cells may be infected with influenza virus (strain A/PR/8/34) in place of rhinovirus. Culture supernatant is harvested 48 and 72 hour post-infection and tested by ELISA for cytokine as described above.

Cells and Virus: Influenza A/PR/8/34 sub type H1N1 (VR-95 American Type Culture Collection, Rockville, Md.) is grown in the allantoic cavity of 10 day old chicken eggs. Following incubation at 37° C., and refrigeration for 2½ hours at 4° C., allantoic fluid is harvested, pooled, and centrifuged (1,000 rcf; 15 min; 4° C.) to remove cells. Supernatent is aliquoted and stored at −70° C. The titer of the stock culture of virus is $1.0 \times 10^{10}$ Tissue Culture Infective Dose/ml ($TCID_{50}$)

Inoculation procedure: Four-six week old female Balb/cAnNcrlBr mice are obtained from Charles River, Raleigh, N.C. Animals are infected intranasally. Mice are anesthetized by intraperitoneal injection of Ketamine (40 mg/kg; Fort Dodge Labs, Fort Dodge, Iowa) and Xylazine (5 mg/kg; Miles, Shawnee Mission, Kans.) and then inoculated with 100 TCID50 of $PR_8$ diluted in PBS in 20 ul. Animals are observed daily for signs of infection.

Virus titration: At various times post infection, animals are sacrificed and lungs are aseptically harvested. Tissues are homogenized, in vials containing 1 micron glass beads (Biospec Products, Bartlesville, Okla.) and 1 ml. of Eagles minimal essential medium. Cell debris is cleared by centrifugation at 1,000 rcf for 15 minutes at 4° C., and supernatants are serially diluted on Madin-Darby canine kidney (MDCK) cells. After 5 days of incubation at 37° C. (5% $CO_2$), 50 μl of 0.5% chick red blood cells are added per well, and agglutination is read after 1 hour at room temperature. The virus titer is expressed as 50% tissue culture infective dose ($TCID_{50}$) calculated by logistic regression.

ELISA: Cytokine levels are measured by quantitative ELISA using commercially available kits. Ear samples are homogenized using a tissue minser in PBS. Cell debris is cleared by centrifugation at 14,000 rpm for 5 minutes. The cytokine concentrations and thresholds are determined as described by the manufacturer; IL-6, IFN-γ, and KC (R&D Systems, Minneapolis, Minn.).

Myeloperoxidase Assay: Myeloperoxidase (MPO) activity is determined kinetically as described by Bradley et al. (1982). Briefly, rabbit cornea are homogenized in Hexadecyl Trimethyl-Ammonium Bromide (HTAB) (Sigma Chemical Co. St. Louis, Mo.) which is dissolved in 0.5 m Potassium phosphate buffer (J. T. Baker Scientific, Phillipsburg, N.J.). Following homogenization, the samples are subjected to freeze-thaw-sonication (Cole-Parmer 8853, Cole-Parmer, Vernon Hills, Ill.) 3 times. Suspensions are then cleared by centrifugation at 12,500×g for 15 minutes at 4° C. MPO enzymatic activity is determined by colormetric change in absorbance during a reaction of O-Dianisidine dihydrochloride (ODI) 0.175 mg/ml (Sigma Chemical Co. St. Louis, Mo) with .0002% Hydrogen peroxide (Sigma Chemical Co. St. Louis, Mo.). Measurements are performed by using a Beckman Du 640 Spectrophotometer (Fullerton, Calif.) fitted with a temperature control device. 50 ul of material to be assayed is added to 950 ul of ODI and change in absorbance is measured at a wave length of 460 nm for 2 minutes at 25° C.

Whole Body Plethysomography: Influenza virus infected mice are placed into a whole body plethysomograph box with an internal volume of approximately 350-ml. A bias airflow of one 1/min is applied to the box and flow changes were measured and recorded with a Buxco XA data acquisition and respiratory analysis system (Buxco Electronics, Sharon, Conn.). Animals are allowed to acclimate to the plethysmograph box for 2 min. before airflow data is recorded. Airway measurements are calculated as Penh (enhanced pause). Penh has previously been shown as an index of airway obstruction and correlates with increased intrapleural pressure. The algorithm for Penh calculation is as follows: Penh=[(expiratory time/relaxation time)-1]× (peak expiratory flow/peak inspiratory flow) where relaxation time is the amount of time required for 70% of the tidal volume to be expired.

Determination of arterial oxygen saturation. A Nonin veterinary hand held pulse oximeter 8500V with lingual sensor (Nonin Medical, Inc., Plymouth Minn.) is used to determine daily arterial oxygen saturation % SpO2 as described (Sidwell et al. 1992 Antimicrobial Agents and Chemotherapy 36:473–476).

Results:

Inhibition of cytokine production by specific inhibitors of p38 MAP kinase:

Consistent with published reports, IL-6, IL-8, and GM-CSF are detected 72 hours post-infection of BEAS-2B cells with rhinovirus-39 (multiplicity of infection; MOI 1.0) (FIG. 1). Production of IL-6, IL-8, and GM-CSF is not mediated through IL-1 or TNF produced in response to rhinovirus infection since addition of neutralizing antibodies to IL-1 and TNF to the infected cultures did not reduce the amount of IL-6, IL-8 or GM-CSF produced (not shown). Productive infection of cells is confirmed by titering infectious supernatants from BEAS-2B cells on HELA monolayers. There is low but consistent replication of virus during the 72 hour culture period resulting in 1.22±0.3 $\log_{10}$ $TCID_{50}$ increase over the initial input inoculum (n=6 experiments).

To investigate the role of p38 kinase signal transduction in rhinovirus-induced cytokine production by epithelial cells, specific p38 kinase inhibitors of Formula (I) may be tested for their ability to inhibit cytokine production in the rhinovirus-infected BEAS-2B cell cultures.

Further data on this method may be found in PCT application U.S. Ser. No. 00/125386, filed Sep. 15, 2000 whose disclosure is incorporated herein by reference in its entirety.

Figure 3:
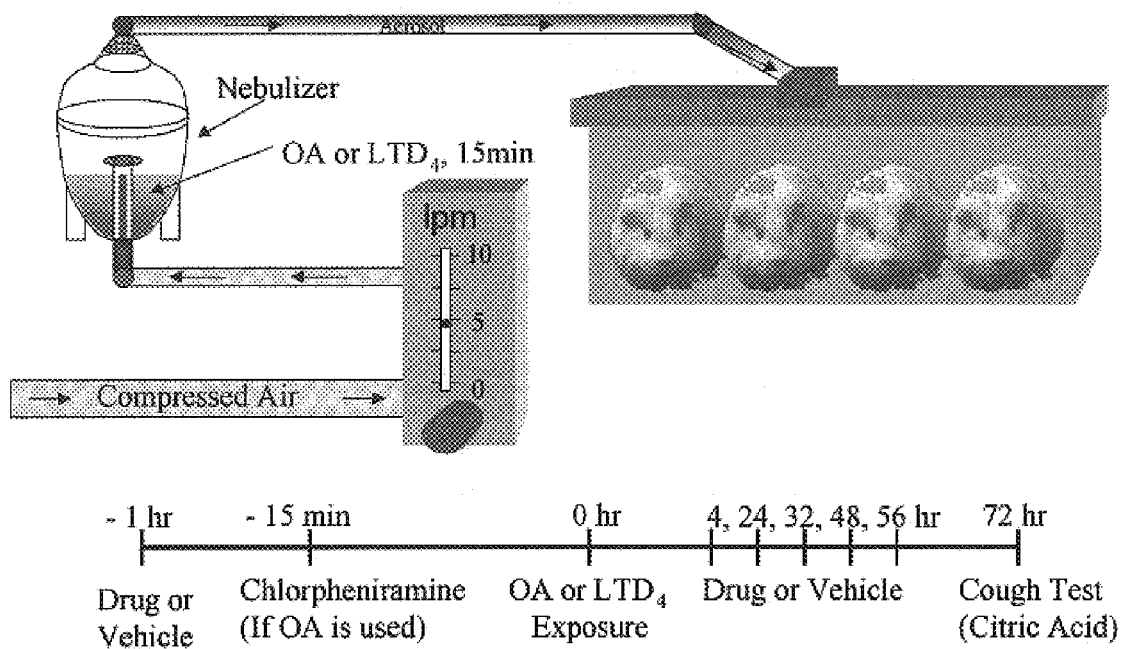
FIG. 3 demonstrates an Antigen- or LTD4-Induced Hypertussive Model in the Guinea Pig FIG. 4 demonstrates Effects of Dextromethorphan or Codeine On Citric Acid-Induced Cough in Guinea Pigs.

Activation of p38 kinase by rhinovirus infection:

The presence of tyrosine phosphorylated p38 kinase is measured by inmmunoblot at various times after the addition of virus to BEAS-2B cultures. Rhinovirus infection of BEAS-2B cells results in an increase in phosphorylated p38 kinase that was both dose and time-dependent. Increases in phosphorylated p38 kinase is evident by 15 minutes post exposure to rhinovirus-39 (MOI 10), appeared to peak by 30 minutes after addition of virus and remained elevated 60 minutes post-infection (FIG. 3). In addition, rhinovirus-induced tyrosine phosphorylation of p38 kinase was dose-dependent. When cells are cultured in the absence of virus, there was no increase in the amount of tyrosine phosphorylation of p38 kinase at any of the timepoints tested. Overall levels of p38 kinase protein were comparable between all the groups indicating that virus infection caused phosphorylation of p38 kinase without de novo synthesis of protein.

Effects on in vitro influenza virus infection:

Exposure of BEAS-2B cells with influenza virus (A/PR/8/34; MOI 1.0) also results in elaboration of IL-8 and IL-6 as measured 48–72 hours post-infection, although the secreted protein levels are lower than that obtained with rhinovirus infection.

Cigarette Smoke Exposure Model

A murine model of cigarette smoke inhalation was developed to explore a relationship to leukocyte trafficking and lung chemokine and cytokine production. Balb/c mice are exposed to smoke generated from commercial unfiltered cigarettes for a specified period of time and samples are obtained at varying times during the post-exposure. This model is demonstrated in greater detail as shown below, in contrast to other smoke extract models known in the art.

A model of cigarette smoke exposure in the mouse is established in which mice are placed 6 at a time into a small animal plexiglass dosing chamber attached to a peristaltic pump whose intake is connected to a holder for a commercial unfiltered cigarette (Lucky Strike™). Along with fresh air, smoke is delivered into the chamber until the cigarette is consumed (approximately 5 minutes). Varying numbers of cigarettes (2–4 per day, 2–3 hr apart) are utilized for 1–3 consecutive days. Animals are euthanized by pentobarbital overdose approximately 18 hours after the final exposure. Bronchoalveolar lavage with phosphate-buffered saline is performed for inflammatory cell enumeration, and BAL aliquots and lungs .are frozen for cytokine analysis. Smoke exposure results in time- and cigarette number-related increases in airway neutrophils, and lung chemokine (KC) and cytokine (IL-6) content.

To evaluate the role of a p38 MAP kinase inhibitor in this inflammatory response, mice are treated with a p38 kinase inhibitor, a compound of Formula (I) at approximatetly a 30 mg/kg, p.o. b.i.d. Reduction in lung KC (a murine homolog of IL-8) levels are assesed 1 day after exposure (prior to neutrophilia), and attenuated airway neutrophilia and lung IL-6 levels are assessed following 3 days of cigarette exposure.

Hypertussive Cough Models

Described below is an example of how to determine the usefulness of p38 inhibitors in the treatment of hypertussive disorders or inflammation enhanced cough.

Figure 2:
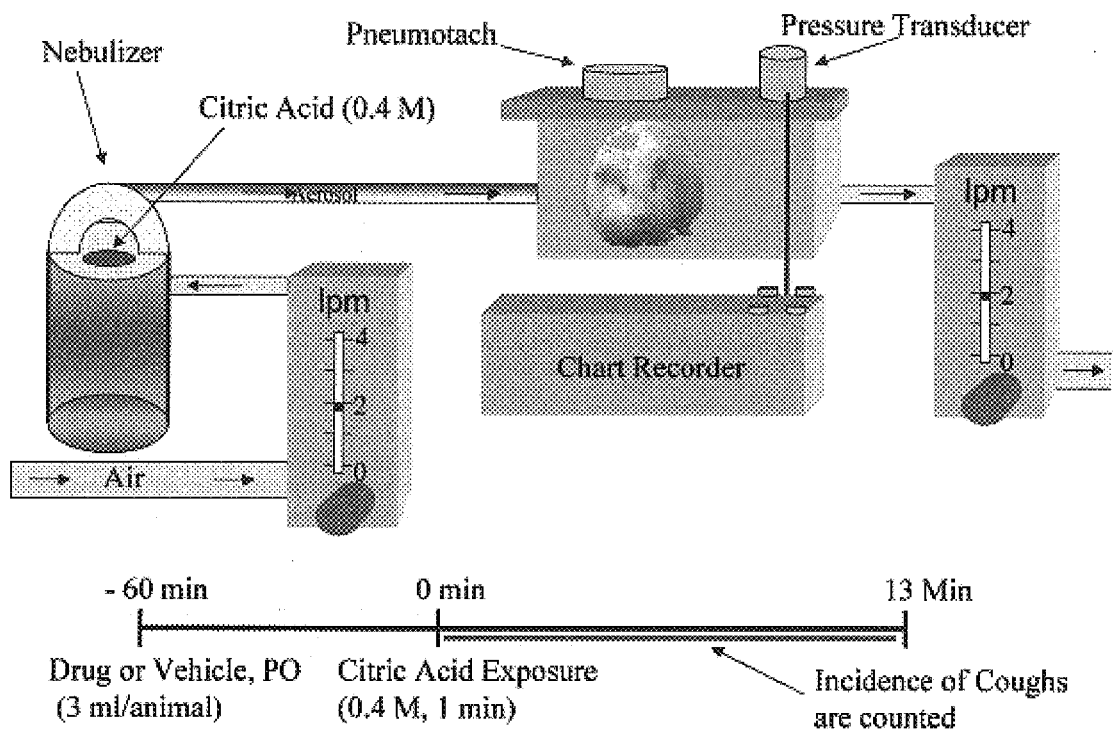
FIG. 2 demonstrates a Citric Acid Induced Cough Model.

The directed antitussive activity of the compound in question if first assessed, by a 10 to 30 minute pretreatment period by intraperitoneal injection or a 1 hour pretreatment period for oral administration. The animals (guinea pigs) are then subjected to an inhaled citric acid-induced cough challenge. The Citric Acid Induced Cough Model is shown in FIG. 2.

The effects of the compound are then assessed on the hypertussive response that occurs 72 hours post aerosol exposure to antigen or LTD4 exposure. Treatment of the animals occurs with the drug prior and/or after antigen or LTD4 challenge, but not on the day of citric acid challenge. The antigen or LTD4 induced hypertussive model is shown in FIG. 3.

Figure 4:
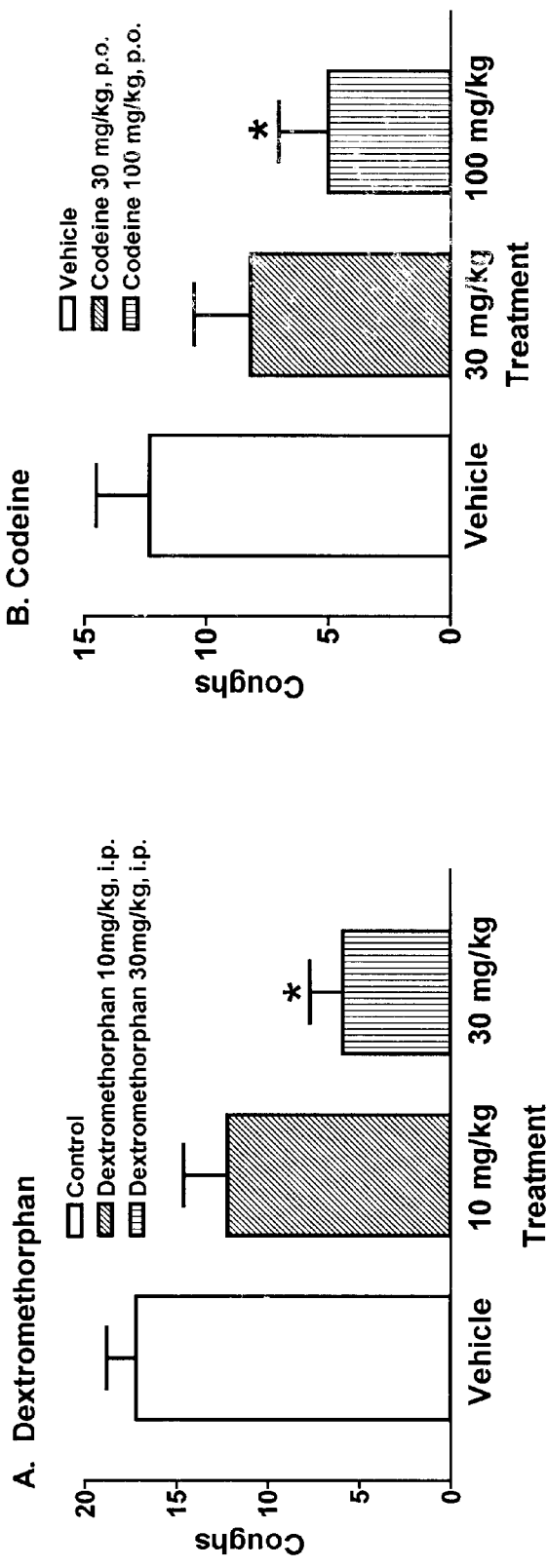

The effects of known antitussive agents, dextromethorphan and codeine on Citric Acid Induced Cough in Guinea Pigs is shown in FIG. 4.

Inhalation of citric acid (CA; 0.4% for 1 minute) induces 11 to 15 coughs during the exposure and 12-minute monitoring period in conscious guinea pigs. Exposure of sensitized animals to inhaled ovalbumin resulted in a hypertussive state (50–80% increae in CA-induced cough incidence) for several days, which positively correlated with airway esoinophilia determined by bronchoalveolar lavage.

Similarly, inhalation of LTD4 (10 ug/ml for 1 minute) increases cough incidence and airway esoinophils 72 hours after exposure.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment or on a micromass platform electrospray ionization mass spectrometer in the positive ion mode using 95:5 $CH_3CN/CH_3OH$ with 1% formic acid as the carrier solvent, unless otherwise indicated. $^1H$-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (23–400 mesh).

Example 1

1-Cyclohexyl-5-phenyl-3.4-dihydro-(1H)-guinazolin-2-one a) 2-Fluoro-6-phenylbenzonitrile The compound, 2-Bromo-6-fluorobenzonitrile, the procedure for the preparation of which may be found in Hynes, John B. et. al., *J. Hetercycl. Chem.* 1988, 25, 1173–7, (2.0 g, 10.0 mmol) and phenylboronic acid (3.66 g, 30 mmol) were added to a mixture of toluene (80 mL), methanol (20 mL), and 2 M aqueous sodium carbonate (20 mL). This mixture was refluxed while stirring under argon for 15 min. The resulting mixture was cooled to room temperature and tetrakis(triphenylphosphine)palladium(0) (1.16 g, 1 mmol) was added. The resulting mixture was then refluxed for 12 hours while stirring under argon. The solvent was removed in vacuo and the residue was partitioned between ethyl acetate and water. The organic phase was washed with water (2×), brine (1×), dried over anhydrous $Na_2SO_4$, filtered, and evaporated to give the crude product which was then chromatographed on silica gel eluted with 0–10% methylene chloride in hexane. Recrystallization from methylene chloride hexane gave the title product as a white crystalline solid. mp 78–79° C.

b) 2-Cyclohexylamino-6-phenylbenzonitrile

The product of example 1a above, 2-fluoro-6-phenylbenzonitrile, (0.1 g, 0.51 mmol), and cyclohexylamine (1 mL) were combined in a sealed tube that had been flushed with argon. The tube was heated in an oil bath to 100° C. for 1.6 hours. The excess cyclohexylamine was evaporated, and the residue was flash chromatographed on silica gel eluted with 0–2% ethyl acetate in hexane, and then recrystallized from methylene chloride/hexane to give the title product as a white crystalline product. mp 125–126° C.

c) 2-Cyclohexylamino-6-(phenyl)benzylamine

The product of example 1b above, 2-cyclohexylamino-6-phenylbenzonitrile, (0.095 g, 0.34 mmol) was dissolved in dry tetrahydrofuran (20 mL) and stirred under argon at room temperature. Lithium aluminum hydride (0.136 g, 3.4 mmol) was added and the mixture heated to reflux under argon for 9 hours. The reaction mixture was cooled to room temperature and anhydrous sodium sulfate was added followed by the addition of a freshly prepared saturated solution of anhydrous sodium sulfate. The solvent was evaporated and the residue triturated with ethyl acetate, filtered and evaporated. Flash chromatography on silica gel eluted with 0–2% methanol in methylene chloride followed by recrystallization from ethyl acetate/hexane gave the title compound as a white crystalline solid. mp 95–96° C.

d) 1-Cyclohexyl-5-phenyl-3,4-dihydro-(1H)-guinazolin-2-one

The product of example 1c above, 2-cyclohexylamino-6-(phenyl)benzylamine, (0.060 g, 0.21 mmol) was dissolved in methylene chloride (10 mL) and cooled in an ice bath while stirring under argon. Phosgene, 20% in toluene, (0.13 mL, 0.25 mmol) was added followed by triethylamine (0.7 mL). The ice bath was removed and the mixture stirred for 30 minutes at room temperature. The solvents were evaporated, and the residue was partitioned between ethyl acetate and water. The organic phase was washed with brine, dried over anhydrous $Na_2SO_4$ filtered, and evaporated to give the crude product which was recrystallized from methylene chloride/hexane to give the title compound as a white crystalline compound. mp 229–231° C.

Example 2

1-Isopropyl-5-phenyl-3,4-dihydro-(1H)-quinazolin-2-one a) 2-Isopropylamino-6-phenylbenzonitrile The product of example 1a above, 2-fluoro-6-phenylbenzonitrile, (0.12 g, 0.61 mmol), and isopropylamine (3 mL) were combined in a sealed tube that had been flushed with argon. The tube was heated in an oil bath to 95° C. for 7 days. The excess isopropylamine was evaporated, and the residue was flash chromatographed on silica gel eluted with 0–3% ethyl acetate in hexane, and then crystallized from hexane to give the title product as a white crystalline product. ES (+) MS m/e=237 (MH+)

b) 2-Isopropylamino-6-(phenyl)benzylamine

The product of example 2a above, 2-isopropylamino-6-phenylbenzonitrile, (0.095 g, 0.4 mmol) was dissolved in dry tetrahydrofuran (20 mL) and stirred under argon at room temperature. Lithium aluminum hydride (0.160 g, 4 mmol) was added and the mixture heated to reflux under argon for 16 hours. The reaction mixture was cooled to room temperature and anhydrous sodium sulfate was added followed by the addition of a freshly prepared saturated solution of anhydrous sodium sulfate. The solvent was evaporated and the residue triturated with ethyl acetate, filtered and evaporated. Flash chromatography on silica gel eluted with 0–3% methanol in methylene chloride followed by recrystallization from ethyl acetate/hexane gave the title compound as a white crystalline solid. ES (+) MS m/e=241 (MH+)

c) 1-Isopropyl-5-phenyl-3,4-dihydro-(1H)-guinazolin-2-one

The product of example 2b above, 2-isopropylamino-6-(phenyl)benzylamine, (0.090 g, 0.37 mmol) was dissolved in methylene chloride (10 mL) and cooled in an ice bath while stirring under argon. Phosgene, 20% in toluene, (0.235 mL, 0.45 mmol) was added followed by triethylamine (1.0 mL). The ice bath was removed and the mixture stirred for 30 minutes at room temperature. The solvents were evaporated, and the residue was partitioned between ethyl acetate and water. The organic phase was washed with brine, dried over anhydrous $Na_2SO_4$ filtered, and evaporated to give the crude product which was recrystallized from methylene chloride/hexane to give the title compound as a white crystalline compound. mp 182–183° C.

Example 3

(+/−)-1-[1-(Phenyl)ethyl]-5-phenyl-3,4-dihydro-(1H)-guinazolin-2-one a) (+/−)-2-[(1-phenyl)ethylamino]-6-phenylbenzonitrile The product of example 1a above, 2-fluoro-6-phenylbenzonitrile, (0.118 g, 0.6 mmol), and (+/−)-1-(phenyl)ethylamine (0.5 mL) were combined in a sealed tube that had been flushed with argon. The tube was heated in an oil bath to 120° C. for 18 hours. The reaction was not complete at this time, so the reaction was heated at 150° C. for an additional 48 hours. Flash chromatography on silica gel eluted with 0–3% ethyl acetate in hexane gave the title product. ES (+) MS m/e=299 (MH+)

b) (+/−)-2-[(1-phenyl)ethylamino]-6-(phenyl)benzylamine

The product of example 3a above, (+/−)-2-[(1-phenyl)ethylamino]-6-phenybenzonitrile, (0.13 g, 0.43 mmol) was dissolved in dry tetrahydrofuran (10 mL) and stirred under argon at room temperature. Lithium aluminum hydride (0.172 g, 4.3 mmol) was added and the mixture heated to reflux under argon for 20 hours. The reaction mixture was cooled to room temperature and anhydrous sodium sulfate was added followed by the addition of a freshly prepared saturated solution of anhydrous sodium sulfate. The solvent was evaporated and the residue triturated with ethyl acetate, filtered and evaporated. Flash chromatography on silica gel eluted with 0–3% methanol in methylene chloride followed by recrystallization from ethyl acetate/hexane gave the title compound as a white crystalline solid. ES (+) MS n/e=303 (MH+)

c) (+/−)-1-[1-(Phenyl)ethyl]-5-phenyl-3,4-dihydro-(1H)-guinazolin-2-one

The product of example 3b above, (+/−)-2-[1-(Phenyl)ethylamino-6-(phenyl)benzylamine, (0.121 g, 0.4 mmol) was dissolved in methylene chloride (10 mL) and cooled in an ice bath while stirring under argon. Phosgene, 20% in toluene, (0.25 mL, 0.48 mmol) was added followed by triethylamine (1.0 mL). The ice bath was removed and the mixture stirred for 30 minutes at room temperature. The solvents were evaporated, and the residue was partitioned between ethyl acetate and water. The organic phase was washed with brine, dried over anhydrous $Na_2SO_4$ filtered, and evaporated to give the crude product which was recrystallized from methylene chloride/hexane to give the title compound as a white crystalline solid. mp 169–171° C.

Example 4

(R)-1-[1-(Phenyl)ethyl]-5-phenyl-3,4-dihydro-(1H)-guinazolin-2-one

Following the procedures of example 3 except for substituting (R)-1-(phenyl)ethylamine for (+/−)-1-(phenyl)ethylamine in step 3a gave the title compound as a white crystalline solid. mp 131–134° C.

Example 5

(S)-1-[1-(Phenyl)ethyl]-5-phenyl-3,4-dihydro-(1H)-guinazolin-2-one

Following the procedures of example 3 except for substituting (S)-1-(phenyl)ethylamine for (+/−)-1-(phenylethylamine in step 3a gave the title compound as a white crystalline solid. mp 136–138° C.

Example 6

1-(2-Phenethyl)-5-phenyl-3,4-dihydro-(1H)-guinazolin-2-one

Following the procedures of example 3 except for substituting 2-phenylethylamine for (+/−)-1-(phenyl)ethylamine in step 3a gave the title compound as a white crystalline solid. mp 152–153° C.

Example 7

1-Benzyl-5-phenyl-3,4-dihydro-(1H)-guinazolin-2-one a) 2-Benzylamino-6-phenylbenzonitrile

The product of example 1a above, 2-fluoro-6-phenylbenzonitrile, (0.118 g, 0.6 mmol), and benzylamine (0.5 mL) were combined in a sealed tube that had been flushed with argon. The tube was heated in an oil bath to 150° C. for 24 hours. The residue was dissolved in methylene chloride (10 mL) and treated with an excess of polystyrene supported isocyanate resin for 30 minutes to remove the excess benzylamine. Filtration and evaporation gave the title product. ES (+) MS m/e=285 (MH+)

b) 2-Benzylamino-6-(phenyl)benzylamine

The product of example 7a above, 2-benzylamino-6-phenylbenzonitrile, was dissolved in dry tetrahydrofuran (10 mL) and stirred under argon at room temperature. Lithium aluminum hydride (0.175 g, 4.3 mmol) was added and the mixture heated to reflux under argon for 20 hours. The reaction mixture was cooled to room temperature and anhydrous sodium sulfate was added followed by the addition of a freshly prepared saturated solution of anhydrous sodium sulfate. The solvent was evaporated and the residue triturated with ethyl acetate, filtered and evaporated to give the title compound. ES (+) MS m/e=272(M-NH2+)

c) 1-Benzyl-5-phenyl-3,4-dihydro-(1H)-guinazolin-2-one

The product of example 7b above, 2-benzyl-6-(phenyl)benzylamine, (assumed 0.4 mmol) was dissolved in methylene chloride (10 mL) and cooled in an ice bath while stirring under argon. Phosgene, 20% in toluene, (0.376 mL, 0.72 mmol) was added followed by triethylamine (2.0 mL). The ice bath was removed and the mixture stirred for 30 minutes at room temperature. The solvents were evaporated, and the residue was partitioned between ethyl acetate and water. The organic phase was washed with brine, dried over anhydrous $Na_2SO_4$ filtered, and evaporated to give the crude product which was flash chromatographed on silica gel eluted with 0–2% methanol in methylene chloride, and then recrystallized from methylene chloride/hexane to give the title compound as a white crystalline solid. mp 198–199° C.

Example 8

1-(2-Morpholin-4yl-ethyl-5-phenyl-3,4-dihydro-(1H)-guinazolin-2-one

The product of example 1a above, 2-fluoro-6-phenylbenizonitrile, (0.118 g, 0.6 mmol), and 4-(2-aminoethyl)morpholine (0.5 mL) were combined in a sealed tube that had been flushed with argon. The tube was heated in an oil bath to 150° C. for 24 hours. Most of the excess amine was removed in vacuo. The residue was taken up in tetrahydrofuran (10 mL), treated with lithium aluminum hydride (0.175 g, 4.3 mmol), and the mixture heated to reflux under argon for 20 hours. The reaction mixture was cooled to room temperature and anhydrous sodium sulfate was added followed by the addition of a freshly prepared saturated solution of anhydrous sodium sulfate. The solvent was evaporated and the residue triturated with ethyl acetate, filtered and evaporated. The residue was taken up in methylene chloride (5 mL) and cooled in an ice bath while stirring under argon. Phosgene, 20% in toluene, (0.375 mL, 0.72 mmol) was added followed by triethylamine (2.0 mL). The ice bath was removed and the mixture stirred for 30 minutes at room temperature. The solvents were evaporated, and the residue was partitioned between ethyl acetate and water. The organic phase was washed with brine, dried over anhydrous $Na_2SO_4$ filtered, and evaporated to give the crude product which was flash chromatographed on silica gel eluted with 0–2% methanol in methylene chloride, and then recrystallized from methylene chloride/hexane to give the title product. mp 228–229° C.

Example 9

1-[2-(2-Pyridinyl)ethyl]-5-phenyl-3,4-dihydro-(1H)-quinazolin-2-one Trifluoroacetate

Following the procedure of example 8 except for substituting 2-(2-pyridinyl)ethylamine for 4-(2-aminoethyl) morpholine and purification by reverse phase hplc purification using an acetonitrile/water/+0.1%trifluoroacetic acid gradient instead of flash chromatography on silica gel gave the title compound. ES (+) MS m/e=330 (MH+)

Example 10

1-(2-Morpholin4-yl-propyl)-5-phenyl-3,4-dihydro-(1H)-guinazolin-2-one Trifluoroacetate

Following the procedure of example 8 except for substituting 4-(3-aminopropyl)morpholine for 4-(2-aminoethyl) morpholine and purification by reverse phase hplc purification using an acetonitrile/water/+0.1%trifluoroacetic acid gradient instead of flash chromatography on silica gel gave the title compound. ES (+) MS m/e=352 (MH+)

Example 11

1-(1-Methylpyrrol-2-ylethyl)-5-phenyl-3,4-dihydro-(1H)-guinazolin-2-one

Following the procedure of example 8 except for substituting 1-methylpyrrol-2-ylethylamine for 2-morpholin-4-yl-ethylamine gave the title compound. mp 158–161° C.

Example 12

1,5-Diphenyl-3,4-dihydro-(1H)-quinazolin-2-one a) 2-Fluoro-6-phenylbenzonitrile The compound, 2-Bromo-6-fluorobenzonitrile, the procedure for the preparation of which may be found in Hynes, John B. et. al., *J. Hetercycl. Chem.* 1988, 25, 1173–7, (2.0 g, 10.0 mmol) and phenylboronic acid (3.66 g, 30 mmol) were added to a mixture of toluene (80 mL), methanol (20 mL), and 2 M aqueous sodium carbonate (20 mL). This mixture was refluxed while stirring under argon for 15 min. The resulting mixture was cooled to room temperature and tetrakis(triphenylphosphine)palladium(0) (1.16 g, 1 mmol) was added. The. resulting mixture was then refluxed for 12 hours while stirring under argon. The solvent was removed in vacuo and the residue was partitioned between ethyl acetate and water. The organic phase was washed with water (2×), brine (1×), dried over anhydrous $Na_2SO_4$, filtered, and evaporated to give the crude product which was then chromatographed on silica gel eluted with 0–10% methylene chloride in hexane. Recrystallization from methylene chloride hexane gave the title product as a white crystalline solid. mp 78–79° C.

b) 2-Phenylamino-6-phenylbenzonitrile

Aniline (0.168 g, 1.8 mmol) was dissolved in dimethyl sulfoxide (3 mL) and stirred under argon at room temperature. Sodium hydride (0.0043 g, 1.8 mmol) was added and a deep purple color developed while the mixture was stirred at room temperature for 1 hour. The mixture was cooled to 0° C. in an ice bath and the product of example 12a above, 2-fluoro-6-phenylbenzonitrile, (0.295 g, 1.5 mmol) dissolved in dimethyl sulfoxide (2 mL) was added and the mixture stirred at room temperature overnight. The solvent was evaporated in vacuo, and the residue was partitioned between ethyl acetate and water. The organic phase was washed with water (5×), brine (1×) dried over anhydrous $Na_2SO_4$ filtered, and evaporated to give the crude product which was then chromatographed on silica gel eluted with 0–30% $CH_2Cl_2$ in hexane to give the title compound as a white amorphous solid. ES (+) MS m/e=271 (MH+)

c) 2-Phenyl-6-(phenylamino)benzylamine

The product of example 1b above, 2-phenylamino-6-phenylbenzonitrile, (0.13 g, 0.48 mmol) was dissolved in dry tetrahydrofuran (20 mL) and stirred under argon in a room temperature water bath. Lithium aluminum hydride (0.182 g, 4.8 mmol) was added rapidly. After 5 minutes at room temperature the reaction mixture was heated to 60° C. for 2 hours. The reaction mixture was cooled to room temperature and anhydrous sodium sulfate was added followed by the addition of a freshly prepared saturated solution of anhydrous sodium sulfate. The solvent was evaporated and the residue triturated with ethyl acetate, filtered and evaporated. Flash chromatography on silica gel eluted with 0–2% methanol in methylene chloride gave the title compound as a white amorphous solid. mp 115–116° C.

d) 1.5-Diphenyl-3,4-dihydro-(1H)-guinazolin-2-one

The product of example 12c above, 2-Phenyl-6-(phenylamino)benzylamine, (0.095 g, 0.35 mmol)was dissolved in dry tetrahydrofuran (3 mL) and stirred under argon at room temperature. 1,1'-Carbonyldiimidazole (0.073 g, 0.45 mmol) dissolved in dry tetrahydrofuran (2 mL) was added and the mixture stirred at room temperature overnight. The solvent was evaporated in vacuo, to give the crude product which was flash chromatographed on silica gel eluted with 0–2% methanol in methylene chloride to give to the title compound as a white amorphous solid. mp 234–235° C.

Example 13

1-(2,6-Difluorphenyl)-5-phenyl-3,4-dihydro-(1H)-guinazolin-2-one a) 2-[(2,6-Difluorophenyl)amino]-6-phenylbenzonitrile Following the procedure of example 12b above except for using 2,6-difluoroaniline in place of aniline gave the title compound as a white crystalline solid. mp 139–141° C.

b) 1-(2,6-Difluorphenyl)-5-phenyl-3,4-dihydro-(1H)-quinazolin-2-one

Following the procedure of example 1c and 1d above except for using 2-[(2,6-Difluorophenyl)amino]-6-phenylbenzonitrile in place of 2-cyclohexylamino-6-phenylbenzonitrile in step 1c gave the title compound as a white crystalline solid. mp 247–249° C.

Example 14

1-Phenyl-5-(2-methylphenyl)-3,4-dihydro-(1H)-quinazolin-2-one mp 236–238° C.

a) 2-fluoro-6-(2-methylphenyl)benzonitrile

Following the procedure of example 12a except substituting 2-methylphenylboronic acid for phenylboronic acid gave the title compound. mp 57–58° C.

b) 2-Phenylamino-6-(2-methylphenyl)benzonitrile

Following the procedure of example 12b except substituting 2-fluoro-6-(2-methylphenyl)benzonitrile for 2-fluoro-6-phenylbenzonitrile gave the title compound. mp 125–126° C.

c) 2-Phenyl-6-(2-methylphenylamino)benzylamine

Following the procedure of example 12c except substituting 2-phenylamino-6-(2-methylphenyl)benzonitrile for 2-phenylamino-6-phenylbenzonitrile gave the title compound. mp 103–105° C.

d) 1-Phenyl-5-(2-methylphenyl)-3,4-dihydro-(1H)-guinazolin-2-one

Following the procedure of example 12d except substituting 2-phenyl-6-(2-methylphenylamino)benzylamine for 2-phenyl-6-(phenylamino)benzylamine gave the title compound. mp 236–238° C.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

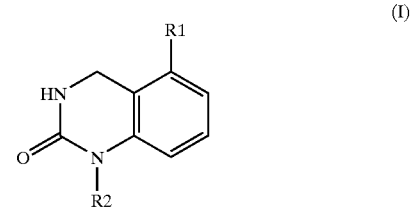

(I)

wherein $R_1$ is a phenyl, naphth-1-yl, naphth-2-yl, or heteroaryl ring, which ring is optionally substituted independently by one or more substituents selected from halogen, $C_{1-4}$ alkyl, halo-substituted-$C_{1-4}$ alkyl, cyano, nitro, $(CR_{10}R_{20})_vNR_4R_{14}$, $(CR_{10}R_{20})_vC(Z)NR_4R_{14}$, $(CR_{10}R_{20})_vC(Z)OR_8$, $(CR_{10}R_{20})_vCOR_3$, $(CR_{10}R_{20})_vC(O)H$, $SR_5$, $S(O)R_5$, $S(O)_2R_5$, $(CR_{10}R_{20})_vOR_8$, $ZC(Z)R_{11}$, $NR_{10}C(Z)R_{11}$, or $NR_{10}S(O)_2R_7$;

$R_2$ is a $C_{1-10}$ alkyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl$C_{1-10}$ alkyl, heteroaryl$C_{1-10}$-alkyl, or heterocyclyl$C_{1-10}$ alkyl moiety, which moiety is optionally substituted one or more times independently with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}OC(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$;

$R_3$ is a $C_{1-4}$ alkyl, halo-substituted $C_{1-4}$ alkyl, $C_{1-4}$ alkenyl, $C_{1-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vNHS(O)_2R_7$, or $(CR_{10}R_{20})_vNR_4R_{14}$; and wherein the aryl, arylalkyl, heteroaryl, or heteroaryl alkyl may be optionally substituted;

$R_4$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_5$ is hydrogen, $C_{1-4}$ alkyl, $C_{2-4}$ alkenyl, $C_{2-4}$ alkynyl or $NR_4R_{14}$, excluding the moieties $SR_5$ being $SNR_4R_{14}$, $S(O)_2R_5$ being $SO_2H$ and $S(O)R_5$ being $SOH$;

$R_6$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or heteroaryl$C_{1-10}$ alkyl, wherein these moieties may be optionally substituted;

$R_7$ is a $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl moiety; and wherein each of these moieties may be optionally substituted;

$R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_t NHS(O)_2R_7$, or $(CR_{10}R_{20})_tNR_4R_{14}$; and wherein the aryl, arylalkyl, heteroaryl, heteroaryl alkyl may be optionally substituted;

$R_9$ is hydrogen, $C(Z)R_6$ or optionally substituted $C_{1-10}$ alkyl, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is a $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_t NHS(O)_2R_7$, or $(CR_{10}R_{20})_vNR_4R_{14}$; and wherein the aryl, arylalkyl, heteroaryl, or heteroaryl alkyl may be optionally substituted;

Z is oxygen or sulfur;

n is 0, or an integer having a value of 1 to 10;

m is 0, or the integer 1 or 2;

v is 0, or an integer having a value of 1 or 2;

t is an integer having a value of 1 to 3;

or a pharmaceutically acceptable salt thereof.

2. The compound according to claim 1 wherein $R_1$ is an optionally substituted phenyl or naphthyl.

3. The compound according to claim 2 wherein the substituent is independently selected from halogen, alkyl, hydroxy, alkoxy, amino, or halosubstituted alkyl.

4. The compound according to claim 3 wherein the substituent is a halogen.

5. The compound according to claim 1 wherein $R_2$ is an optionally substituted, arylalkyl, $C_{3-7}$ cycloalkyl, heteroaryl$C_{1-10}$ alkyl, or heterocyclyl$C_{1-10}$ alkyl.

6. The compound according to claim 5 wherein $R_2$ is an optionally substituted, benzyl, phenethyl, cyclohexyl, pyrrolindylmethyl, morpholino ethyl, morpholinopropyl, $C_{1-4}$ alkyl, or pyridylethyl.

7. The compound according to claim 5 wherein the substitutent is independently halogen, alkyl, hydroxy, alkoxy, amino, or halosubstituted alkyl.

8. The compound according to claim 6 wherein the substituent is a halogen, or alkyl.

9. The compound according to claim 1 which is:

1-Cyclohexyl-5-phenyl-3,4-dihydro-(1H)-quinazolin-2-one;

1-Isopropyl-5-phenyl-3,4-dihydro-(1H)-quinazolin-2-one;

(+/−)-1-[1-(Phenyl)ethyl]-5-phenyl-3,4-dihydro-(1H)-quinazolin-2-one;

(R)-1-[1-(Phenyl)ethyl]-5-phenyl-3,4-dihydro-(1H)-quinazolin-2-one;

(S)-1-[1-(Phenyl)ethyl]-5-phenyl-3,4-dihydro-(1H)-quinazolin-2-one;

1-(2-Phenethyl)-5-phenyl-3,4-dihydro-(1H)-quinazolin-2-one;

1-Benzyl-5-phenyl-3,4-dihydro-(1H)-quinazolin-2-one;

1-(2-morpholin-4-yl-ethyl-5-phenyl-3,4-dihydro-(1H)-quinazolin-2-one;

1-[2-(2-pyridinyl)ethyl]-5-phenyl-3,4-dihydro-(1H)-quinazolin-2-one;

trifluoroacetate 1-(2-morpholin-4-yl-propyl)-5-phenyl-3,4-dihydro-(1H)-quinazolin-2-one;

trifluoroacetate 1-(1-methylpyrrol-2-ylethyl)-5-phenyl-3,4-dihydro-(1H)-quinazolin-2-one;

or a pharmaceutically acceptable salt thereof.

10. A pharmaceutical composition comprising an effective amount of a compound according to claim 1 and a pharmaceutically acceptable carrier or diluent.

11. A method of treating a CSBP/RK/p38 kinase mediated disease in a mammal in need thereof, which method comprises administering to said mammal an effective amount of a compound of Formula (I) according to claim 1.

12. The method according to claim 11 wherein the CSBP/RK/p38 kinase mediated disease is psoriatic arthritis, Reiter's syndrome, gout, traumatic arthritis, rubella arthritis and acute synovitis, rheumatoid arthritis, rheumatoid spondylitis, osteoarthritis, gouty arthritis, sepsis, septic shock, endotoxic shock, gram negative sepsis, toxic shock syndrome, cerebral malaria, meningitis, ischemic and hemorrhagic stroke, neurotrauma/open or closed head injury, asthma, adult respiratory distress syndrome, chronic pulmonary inflammatory disease, chronic obstructive pulmonary disease, silicosis, pulmonary sarcososis, bone resorption disease, osteoporosis, restenosis, cardiac, brain and renal reperfusion injury, thrombosis, glomerularnephritis, chronic renal failure, diabetes, diabetic retinopathy, macular degeneration, graft vs. host reaction, allograft rejection, inflammatory bowel disease, Crohn's disease, ulcerative colitis, neurodegenrative disease, muscle degeneration, diabetic retinopathy, macular degeneration, tumor growth and metastasis, angiogenic disease, eczema, contact dermatitis, psoriasis, sunburn, or conjunctivitis.

13. A method of treating the common cold or respiratory viral infection caused by human rhinovirus (HRV), other enteroviruses, coronavirus, influenza virus, parainfluenza virus, respiratory syncytial virus, or adenovirus in a human in need thereof which method comprises administering to said human an effective amount of a compound of Formula (I) according to claim 1.

14. The method according to claim 13 wherein the respiratory viral infection exacerbates asthma, chronic bronchitis, chronic obstructive pulmonary disease, otitis media, or sinusitis.

15. A method of treatment of smoke induced airway inflammation in a human in need thereof, which comprises administering to said human an effective amount of a compound according to claim 1.

16. The method according to claim 15 wherein the smoke induced airway inflammation is caused by inhalation of cigarette smoke, inhalation of smoke produced from a burning plant material, or inhalation of burning smoke from fossil fuels.

17. The method according to claim 15 wherein the smoke induced airway inflammation exacerbates a pre-existing asthmatic condition, a pre-existing chronic bronchitis, or pre-existing chronic obstructive pulmonary disease in said human.

18. A method of treatment, for inflammation enhanced cough in a mammal in need thereof, which comprises administering to said mammal an effective amount of a compound according to claim 1.

19. The method according to claim 18 wherein the inflammation enhanced cough is cough variant asthma, or eosinophilic bronchitis.

20. The method according to claim 13 wherein the compound of Formula (I) is administered with a second therapeutic agent.

21. The method according to claim 20 wherein the second therapeutic agent is an anti-tussive; an antihistamine; a steroid; a $PDE_4$ agent, an antibiotic; an anti-inflammatory agent selected from an NSAID, a COX-1 or COX-2 inhibitor, ASA, or indomethacin; an antiviral agent ribavirin, amantidine, rimantidine, Pleconaril, AG 7088, or BTA-188; a decongestant; an influenza neuraminidase inhibitor selected from zamanivar (Relenza), oseltamivir (Tamiflu) or RWJ-270201.

22. The method according to any one of claims 13 to 19 wherein the compound of Formula (I) is administered orally, topically (intranasal) or via inhalation (aerosol), or both topically and via inhalation.

23. The method according to claim 15 wherein the compound of Formula (I) is administered with a second therapeutic agent.

24. The method according to claim 23 wherein the second therapeutic agent is an antitussive; an antihistamine; a steroid; a $PDE_4$ agent, an antibiotic; an anti-inflammatory agent selected from an NSAID, a COX-1 or COX-2 inhibitor, ASA, or indomethacin; an antiviral agent ribavirin, amantidine, rimantidine, Pleconaril, AG 7088, or BTA-188; a decongestant; an influenza neuraminidase inhibitor selected from zamanivar (Relenza), oseltamivir (Tamiflu) or RWJ-270201.

25. The method according to any claim 15 wherein the compound of Formula (I) agent is administered orally, topically (intranasal) or via inhalation (aerosol), or both topically and via inhalation.

26. The method according to claim 18 wherein the compound of Formula (I) is administered with a second therapeutic agent.

27. The method according to claim 26 wherein the second therapeutic agent is an antitussive; an antihistamine; a steroid; a $PDE_4$ agent, an antibiotic; an anti-inflammatory agent selected from an NSAID, a COX-1 or COX-2 inhibitor, ASA, or indomethacin; an antiviral agent ribavirin, amantidine, rimantidine, Pleconaril, AG 7088, or BTA-188; a decongestant; an influenza neuraminidase inhibitor selected from zamanivar (Relenza), oseltamivir (Tamiflu) or RWJ-270201.

28. The method according to any claim 18 wherein the compound of Formula (I) agent is administered orally, topically (intranasal) or via inhalation (aerosol), or both topically and via inhalation.

* * * * *

UNITED STATES PATENT AND TRADEMARK OFFICE
CERTIFICATE OF CORRECTION

PATENT NO.    : 6,759,410 B1
DATED         : July 6, 2004
INVENTOR(S)   : Adams et al.

It is certified that error appears in the above-identified patent and that said Letters Patent is hereby corrected as shown below:

Title page,
Item [57], ABSTRACT,
Delete the Abstract, and replace with the following:

-- Novel substituted quinazoline compounds and compositions for use in therapy as CSBP/p38 kinase inhibitors. --

Signed and Sealed this

Twelfth Day of October, 2004

JON W. DUDAS
*Director of the United States Patent and Trademark Office*